US012699083B2

(12) United States Patent
Sun et al.

(10) Patent No.: US 12,699,083 B2
(45) Date of Patent: Aug. 4, 2026

(54) DEVICE FOR CONTINUOUS MEASUREMENT OF CARDIAC ACTIVITY

(71) Applicants:The Hospital for Sick Children, Toronto (CA); The Governing Council of the University of Toronto, Toronto (CA)

(72) Inventors: Yu Sun, Toronto (CA); Jason Maynes, Toronto (CA); Li Wang, Toronto (CA); Wenkun Dou, Toronto (CA); Craig Simmons, Toronto (CA)

(73) Assignees: The Hospital for Sick Children, Toronto (CA); The Governing Council of the University of Toronto, Toronto (CA)

( * ) Notice: Subject to any disclaimer, the term of this patent is extended or adjusted under 35 U.S.C. 154(b) by 1530 days.

(21) Appl. No.: 17/059,385

(22) PCT Filed: May 29, 2019

(86) PCT No.: PCT/CA2019/050729
§ 371 (c)(1),
(2) Date: Nov. 27, 2020

(87) PCT Pub. No.: WO2019/227211
PCT Pub. Date: Dec. 5, 2019

(65) Prior Publication Data
US 2021/0215675 A1      Jul. 15, 2021

Related U.S. Application Data

(60) Provisional application No. 62/677,608, filed on May 29, 2018.

(51) Int. Cl.
*G01N 33/50*      (2006.01)
*G01N 21/64*      (2006.01)
*G01N 27/04*      (2006.01)

(52) U.S. Cl.
CPC ......... *G01N 33/5061* (2013.01); *G01N 21/64* (2013.01); *G01N 27/041* (2013.01)

(58) Field of Classification Search
CPC ... G01N 33/5061; G01N 21/64; G01N 27/041
See application file for complete search history.

(56) References Cited

U.S. PATENT DOCUMENTS

2004/0033482 A1*  2/2004  Artmann ............ G01N 33/5064
                                                    435/287.1
2011/0039294 A1   2/2011  Wang et al.
                          (Continued)

FOREIGN PATENT DOCUMENTS

EP        2 626 411 A1    8/2013
WO      WO-2011/146531 A1   11/2011
WO      WO 2012/017343    *  2/2012

OTHER PUBLICATIONS

International Search Report and Written Opinion on PCT/CA2019/050729 dated Aug. 7, 2019, 15 pages.

*Primary Examiner* — Michael L Hobbs
(74) *Attorney, Agent, or Firm* — Foley & Lardner LLP

(57) ABSTRACT

A device and method for measuring at least one cellular activity. The device includes: (a) a deformable polymeric base membrane having a first side and a second side, the polymeric base including a well having an opening on the first side, a cavity extending from the opening and a floor formed by the second side of the polymeric base membrane, (b) a deformable polymeric top membrane overlapping the second side of the polymeric base membrane; and (c) a sensing element disposed between the polymeric base membrane and the polymeric top membrane, the sensing element being disposed over the floor of the well, such that a portion of the second side that forms the floor of the well, the (Continued)

sensing element and a portion of the top membrane that overlaps the well form a suspended membrane.

14 Claims, 12 Drawing Sheets

(56) References Cited

U.S. PATENT DOCUMENTS

| | | | |
|---|---|---|---|
| 2013/0230911 A1* | 9/2013 | Charest | .................... B29C 59/00 |
| | | | 435/297.1 |
| 2018/0221874 A1* | 8/2018 | Parker | ................ G01N 33/5061 |

* cited by examiner

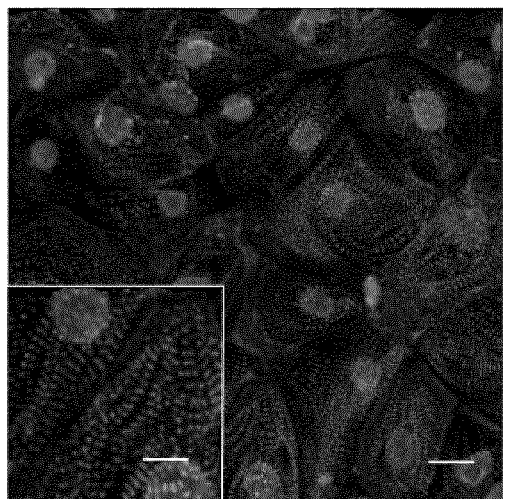
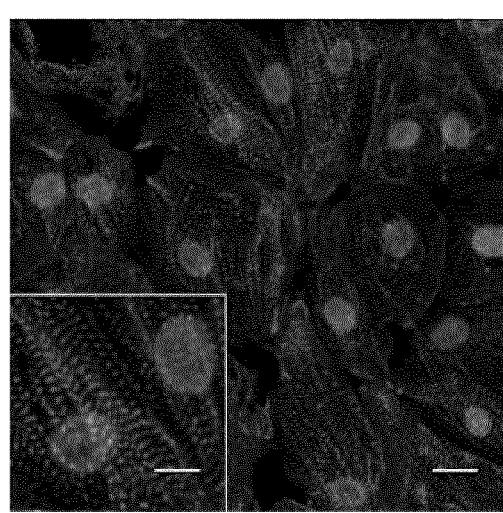
FIG. 11A                                          FIG. 11B

DEVICE FOR CONTINUOUS MEASUREMENT OF CARDIAC ACTIVITY

FIELD

The present invention relates to a device for continuous measurement of cardiac activity. More particularly, to a micro device platform for continuous measurement of contractility, beating rate, and beating rhythm of hiPSC-cardiomyocytes.

BACKGROUND

The heart completes a complex set of tasks, including the initiation or propagation of an electrical signal with regularity (proper heart rate and rhythm), and generating sufficient force of contraction (contractility). Probing mechanisms of heart diseases and quantifying drug efficacies demand a platform that is capable of continuous operation inside a cell incubator for long-term measurement of cardiomyocyte monolayers.

Several techniques have been developed for measuring the contractile stress/force of cardiomyocytes. Table 1 summarizes existing techniques and their working principles. Since 1984, electrical impedance measurement using microelectrode arrays has been used to monitor cell behavior such as growth and spreading. [8] Recently, there have been attempts to utilize impedance signal changes to indicate cardiomyocytes' contractility. [9, 10] Although impedance measurement has inherent capabilities for measuring the beating rate of cardiomyocytes, direct correlations between impedance change and contractile stress generated by cardiomyocytes remain elusive.

TABLE 1

Summary of existing measurement of contractility of cardiomyocytes

| Methods | Cantilever (including AFM) | Microposts | Calcium imaging | Impedance |
|---|---|---|---|---|
| Measurement principle | Cantilever with nanoscale tip probes over cellular substrate to measure contractile forces. | Using high speed microscopy to record the deflection of micropost | fluorescent dyes to quantify $Ca^{2+}$ concentrations in the cytoplasm as an indicator for contractility | Impedance change caused by the distance change between the cells and microelectrode |
| Suitable for monolayer | No | No | Yes | Yes |
| Contractile stress/force range | 1-5 kPa (neonatal rat); 4.6-18 nN (hiPSC-CM); 5 μN (SD rat) | 67 nN to few μN | — | — |
| Advantages | 1) direct force displacement relationship; 2) Response time less than 1 ms AFM only: 1) Commercial accuracy; 2) Other available mechanical properties simultaneously | 1)3D-contractile force available; 2)Other mechanical and physical properties available; | 1) Real high-throughput analyses with up to 1536 samples at a time; 2) Drug screen. | 1) Real time and long-time recording; 2) Drug screen. |
| Disadvantages | 1) Inability to measure the force along XY plane; 2)The accumulated heat scalding cells; 3)Time consuming; 4) Hard to keep cantilevers consistent and high-yield; 5) Inability to incorporated into a high throughput device; AFM only: 1) Invasive and contact for cells. | 1) Affecting cells' morphology and cytoskeletal structure; 2) Time-consuming to optimal stiffness of micropost; 3) Inability to obtain real time contractile force. | 1) Indirect contractility measurements; 2) Damaging cells as residual beads. | 1) An indicator (cell index) to present the contractile force of CMs 2) Potential to induce undesired side effects by the alternating current flow. |
| Reference Methods | [22], [23], [24] Cell Drum | [11], [12], [16] Carbon Fiber | [8], [9], 10] Traction force microscopy | [5], [6], [7] |
| Measurement principle | Cardiomyocytes cultured on the thin silicon membrane to measure cellular pressure. | Carbon fibers attached directly to Cell: 1) monitoring the piezoelectric resistance; 2) recording the deflection of carbon fiber | Frame by frame capture of fluorescent beads used to estimate forces | |
| Suitable for monolayer | Yes | No | No | |

TABLE 1-continued

| | Summary of existing measurement of contractility of cardiomyocytes | | | |
|---|---|---|---|---|
| Methods | Cantilever (including AFM) | Microposts | Calcium imaging | Impedance |
| Contractile stress/force range | 43.1 + 7.5 kPa (hiPSC-CMs) | Less than 5 µN (neonatal rat); | 1.07-3.69 kPa (neonatal rat); 20-100 nN (neonatal rat); 1.69-5.87 kPa(hiPSC-CM); | |
| Advantages | 1) Long time and continuous recording; 2) The culture environment as comfortable as commercial culture plates. | 1) Simultaneous recordings of membrane potential and contractility; 2) Application for evaluating the role of a specific protein in the cardiac function, as CF widely used as a molecular probe. | 1) Ability for analyzing force change during a cycle of diastole and systole; 2) Force distribution of cell's any part can be obtained at any time; 3) Comfortable culture environment for cell; 4) Noninvasive and in situ measurement | |
| Disadvantages | 1) Imprecise pressure measurement, 2) Disposable device, 3) Ultra-thin silicon film, leading to high-cost fabrication | 1) Invasive and contact for cells. 2) Time point recording | 1) Inability to measure vertical contractile force; 2) Random distribution of fluorescent beads, failing to keep consistent resolution for the obtained contractile forces; 3) Time point recording | |
| References | [20], [21] | [18], [19] | [10], [11], [12], [17] | |

For direct contractility measurement, microcantilevers were developed [11, 12] where the deflection of the cantilever caused by cardiomyocyte contraction was measured by detecting the reflection angle change of a laser beam shed onto the backside of the cantilever. Heat generated by laser irradiation in micro-cantilever measurement can cause undesired changes in cell metabolism. [13, 14] Existing laser-based cantilevers also require the devices with cells cultured on them to be moved in and out of cell incubators for performing each measurement. This is undesired since cardiomyocytes' contractility, beating rate, and beating rhythm are highly sensitive to environmental parameters such as temperature and concentration of $CO_2$. [15-17] Laser-based cantilevers fully integrated with measurement components that can achieve long-term, continuous monitoring of cardiomyocyte behaviors remain to be developed.

Piezoresistive cantilevers have recently been reported for measuring contractility of cardiomyocytes by continuously monitoring electrical resistance change inside a controlled incubator environment. [18, 19] The devices were constructed via 3D printing, which required the proper design of six functional inks. The devices were proven effective for continuous, long-term measurement of cardiomyocytes' contractility; however, they had a relatively low sensitivity. Sensitivity of these piezoresistive cantilevers is defined by a ratio between the output (resistance signal, $\Delta R/R_0$) and the input (measured contractile stress). $\Delta R/R_0$ of these devices varied from $6.13 \times 10^{-5}$ to $3.00 \times 10^{-3}$ for per unit stress. [18, 19, 65, 66]

Cell drum has also been reported for measuring the contractility of cardiomyocytes. Cell drum is a flexible membrane device where a thin silicone membrane is sealed on the top of a chamber. [20] Both laser sensor and pressure sensor are assembled inside the sealed chamber for monitoring membrane deflection. A positive pressure is applied through the chamber to keep the silicone membrane flat when cardiomyocytes are seeded on the membrane. The stress caused by cardiomyocyte contraction induces a pressure change inside the chamber and membrane deflection, which are respectively detected by the pressure sensor and the laser sensor. However, the reported contractile stress of hiPSC-CMs measured by the cell drum technique is ten times higher than the values measured with other techniques (43.1±7.5 kPa vs. 3.78±2.09 kPa, see Table 1 and 19, 21, 22). This may be attributed to the poor accuracy of the cell drum measurement due to the very small pressure variations caused by cell contraction, leading to a low signal-to-noise-ratio. [20, 23]

Micropost arrays [24, 25] and hydrogel thin films embedded with fluorescent beads (TFFB) [26-28] have been used as substrates for culturing cardiomyocytes. Micropost or hydrogel film deflections caused by cardiomyocyte contraction are monitored via microscopy imaging and converted into forces via mechanics models. The micropost technique is able to measure contractile force, contractile velocity, and contractile power. [24, 25] However, the topographical patterns of microposts trigger changes in cardiomyocytes' morphology and cytoskeletal structures, cell aggregation, and differentiation. [29] TFFB uses hydrogels and embedded fluorescent beads for measuring cell traction forces and has been employed to measure the contractile force of rat, quail, and hESC-derived cardiomyocytes. [26, 27] Tracking the position changes of a high number of fluorescent beads and analyzing the image data in order to convert the position changes into pressure fields generated by cardiomyocytes are highly time-consuming. [30] Therefore, TFFB technique reported in the literature for cardiomyocyte studies often focused on single-cell measurement. However, no heart cell is in isolation, and investigations on individual cells lose the contributions of cell-to-cell communication, gap junctions, and coordinated cellular action, vital components of heart contractile function.

What is needed is a device that can measure beating rate, rhythm and contractility of a monolayer of hiPSC-CMs that has high sensitivity value, high signal-to-noise ratio, and that does not trigger changes in the cardiomyocytes' morphology, cytoskeletal structures, cell aggregation and differentiation.

SUMMARY

Disclosed is a device for measuring properties of excitable cells, such as beating rate, rhythm, and contractility of a monolayer of hiPSC-CMs. The device of the present invention integrates a sensing element for measuring cardiac activity in cardiomyocytes, such as composites of carbon nanotubes (CNT), and PDMS. Contraction of cardiomyocytes seeded on the device causes changes in the structure of the sensing element network and further the electrical resistance. The present invention provides a device for assessing excitable cells.

As such, in one embodiment, the present invention relates to a device for measuring at least one cellular activity. The device, in one embodiment, includes: (a) a deformable polymeric base membrane having a first side and a second side, the polymeric base including a well, the well having an opening on the first side, a cavity extending from the opening and a floor formed by the second side of the polymeric base membrane, (b) a deformable polymeric top membrane overlapping the second side of the polymeric base membrane; and (c) a sensing element for measuring the at least one cellular activity disposed between the polymeric base membrane and the polymeric top membrane, the sensing element being disposed over the floor of the well, such that a portion of the second side that forms the floor of the well, the sensing element and a portion of the top membrane that overlaps the well form a suspended membrane.

In one embodiment, the device of the present invention further includes a substrate, and wherein the first side of the polymeric base membrane is connected to the substrate.

In another embodiment of the device of the present invention, the polymeric base membrane further includes a hole configured to receive a tubing means, and microchannels connecting the well with the hole.

In another embodiment of the device of the present invention, the device further includes a polymeric ring coupled onto the portion of the top polymeric membrane that forms the suspended membrane.

In another embodiment of the device of the present invention, the device further includes means for measuring an electrical resistance of the sensing element.

In another embodiment of the device of the present invention, the top polymeric membrane further includes embedded beads capable of producing an optical signal.

In another embodiment of the device of the present invention, the embedded beads are fluorescent beads.

In another embodiment of the device of the present invention, the device includes more than one well and more than one sensing elements, each sensing element being disposed over the floor of one well, such that a portion of the second side that forms the floor of the well, the sensing element and a portion of the top membrane that overlaps the well form a number of suspended membranes equal to the number of wells in the device.

In another embodiment of the device of the present invention, the sensing element is selected from a carbon nanotube (CNT), a gold-based, platinum-based, carbon ink, or graphene sensing elements.

In another embodiment of the device of the present invention, the sensing element is a CNT strip, wherein the CNT strip extends over the floor of the well.

In another embodiment, the present invention relates to a method for continuous measuring at least one cellular activity. The method, in one embodiment, includes: (a) providing a device according to any one of the previous embodiments; (b) seeding cells onto the suspended membrane of the device; and (c) continuously measuring an electrical resistance of the sensing element, thereby continuously measuring the cellular activity of the cells. In one aspect the cells are cardiomyocytes.

In one embodiment of the method for continuous measuring at least one cellular activity, the cellular activity is contractility, beating rate or beating rhythm.

In another embodiment, the present invention relates to a method for determining an effect of at least one drug on cells on at least one cellular activity in cardiomyocytes. The method, in one embodiment, includes: (a) providing a device according to any one of the previous embodiments; (b) seeding cells onto the suspended membrane of the device, (c) exposing the cells either before or after being seeded to the at least one drug, (d) continuously measuring an electrical resistance of the sensing element, thereby determining the effect of the at least one drug on the least one cellular activity of the cells. In one aspect the cells are cardiomyocytes.

In one embodiment of the method for determining an effect of at least one drug on cells on at least one cardiac activity, the cellular activity is contractility, beating rate or beating rhythm.

BRIEF DESCRIPTION OF THE DRAWINGS

FIG. 8A is a graph showing resistance signal over time. Resistance signal (R) changed periodically, induced by cyclic air pressures. The mean resistance value reduced to 75 kΩ and reached equilibrium after 24 hours.

FIG. 11A is a confocal image of cells cultured on a Petri-dish. Scale bar: 20 μm; scale bar of inset: 7.5 μm.

FIG. 11B is a confocal image of cells cultured on a device according to one embodiment of the present invention. Scale bar: 20 μm; scale bar of inset: 7.5 μm.

DETAILED DESCRIPTION

Figure 1:
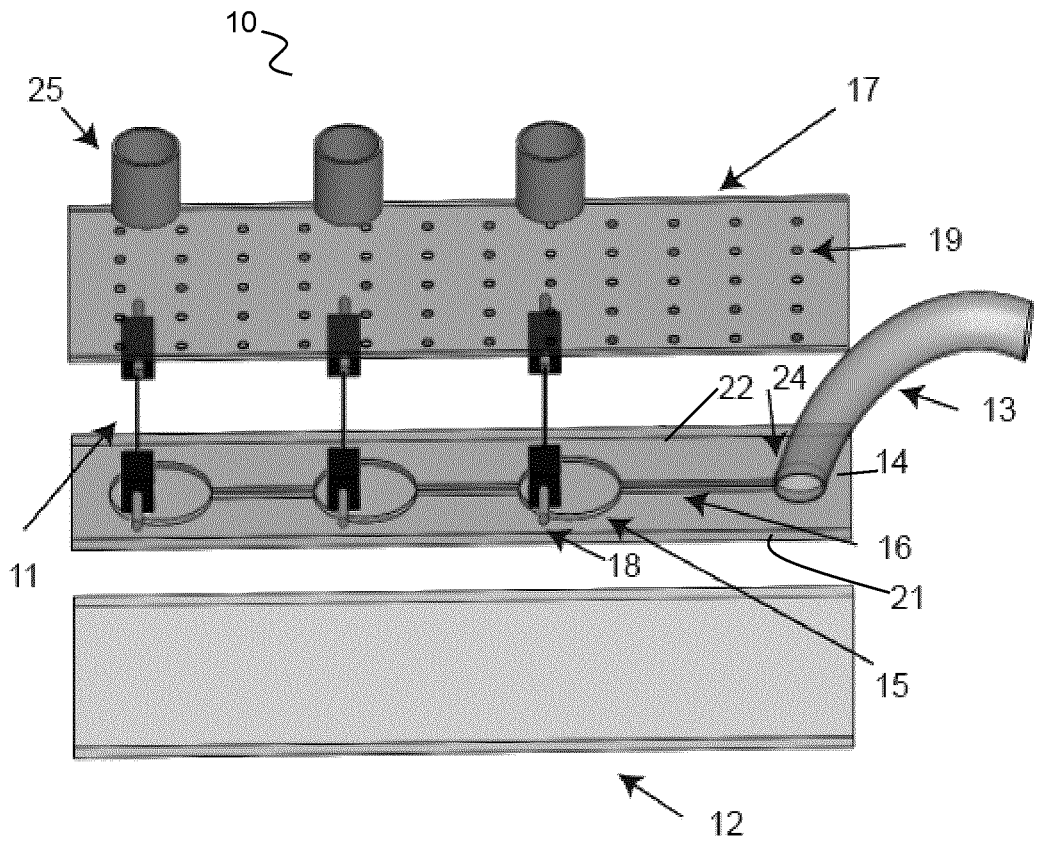
FIG. 1 is an exploded view of the device according to one embodiment of the present invention.

Detailed embodiments are disclosed herein; however, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-19, but the embodiments are not limited to the illustrated structure or application.

In addition, numerous specific details are set forth in order to provide a thorough understanding of the embodiments described herein. However, it will be understood by those of ordinary skill in the art that the embodiments described herein can be practiced without these specific details.

Definitions

The following definitions, unless otherwise stated, apply to all aspects and embodiments of the present application. Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "include without limitation"). Singular forms included in the claims such as "a", "an" and "the" include the plural reference unless expressly stated otherwise. All relevant reference, including patents, patent applications, government publications, government regulations, and academic literature are hereinafter detailed and incorporated by reference in their entireties.

The term "plurality," when used herein, is defined as two or more than two. The term "another," as used herein, is defined as at least a second or more. The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC). The term "substantially" includes exactly the term it modifies and slight variations therefrom.

The term "about" modifying any amount refers to the variation in that amount encountered in real world conditions of producing materials such as polymers or composite materials, e.g., in the lab, pilot plant, or production facility. For example, an amount of an ingredient employed in a mixture when modified by about includes the variation and degree of care typically employed in measuring in a plant or lab and the variation inherent in the analytical method. Whether or not modified by about, the amounts include equivalents to those amounts. Any quantity stated herein and modified by "about" can also be employed in the present invention as the amount not modified by about.

The term "CNT" means carbon nanotubes; "hiPSC-CMs" means human induced pluripotent stem cells-cardiomyocytes; "PDMS" means polydimethylsiloxane, which belongs to a group of polymeric organosilicon compounds that are commonly referred to as silicones.

The cells most suitable for the present invention are those cells which can be cultured under constant and reproducible cell culture conditions, and which grow in culture as an attached monolayer. The cells can be dividing, quiescent or senescent or at any point of viability, ranging from inoculation through death.

The cell type being cultured may be selected for testing based upon whether a drug to be tested is intended for human or veterinary uses, or other uses. The cells can be primary or secondary cultures, differentiated or undifferentiated, transformed, transfected, engineered or recombinant cells, or the like, as applicable to the substance being tested.

"Monolayer" refers to a layer of cells no more than a single cell in depth, preferably attached to portion of the polymeric top membrane that forms the suspended membrane of the device of the present invention.

The preferred cells for use in the present invention are cardiomyocytes, including hiPSC-cardiomyocytes or animal cardiomyocytes.

The Device

The present invention comprises a device and method for continuous measurement of cellular activity. The device of the present invention can be used for determining the effect of a drug on cells grown on the device.

In accordance with the present invention the device can be used to continuous monitor or test the effect of a drug or other medicament on cardiomyocytes. Mammalian cells, especially human cardiomyocytes, are the type which are most often used for drug testing, and so are the type for which this invention is most applicable. However, the invention could also be extended to bird, rodent, fish, amphibian, insect or any other cardiomyocytes that can be grown on the device as a monolayer.

Figure 2A:
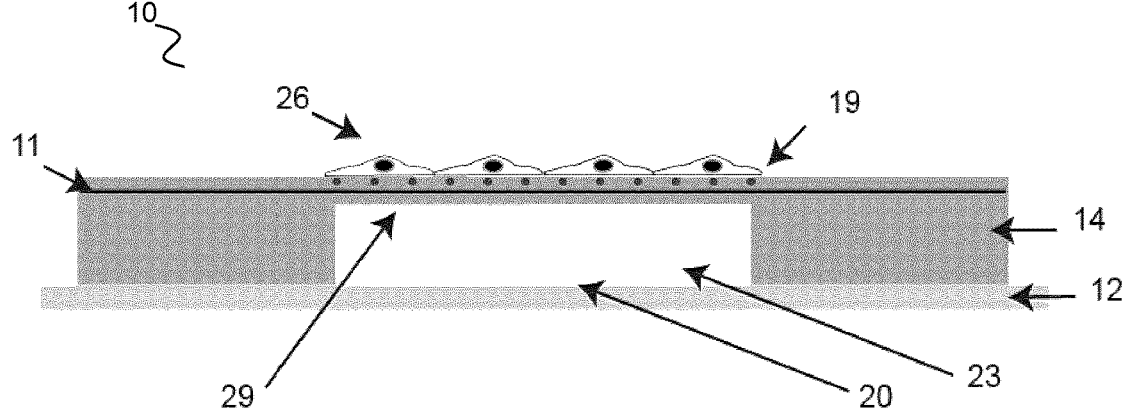
FIG. 2A is a schematic diagram illustrating membrane deflection induced by diastole of monolayer human induced pluripotent cells stem cells-cardiomyocytes (hiPSC-CMs). Under diastolic state, the contractile stress is 0, and, therefore, there is no membrane deflection.

With reference to FIGS. 1 and 2A, a device 10 of the present invention includes, in one embodiment, a polymeric base membrane 14 having a first side 21 and a second side 22, the polymeric base 14 including a well 23 having an opening 20 on the first side 21, a cavity 23 or actuation cavity extending from the opening 20 and a floor 29 formed by the second side 22 of the polymeric base membrane 14. FIG. 1 illustrates a base membrane having three wells, which translates into three suspended membranes, however, one skilled in the art understands that the device may include at least one well. As such the device 10 of the present invention may be considered as an array of suspended membranes. A polymeric top membrane 17 overlaps the second side 22 of the polymeric base membrane 14. Beads 19 that can produce an optical signal may be embedded into the polymeric top membrane 17. A sensing element 11 is disposed between the polymeric base membrane 14 and the polymeric top membrane 17. The sensing element 11, in one embodiment, extends over the floor 29 of the well, such that a portion 15 of the second side 22 that forms the floor 29 of the well, the sensing element 11 and the top membrane 17 that overlaps the well form a suspended membrane. The suspended membrane consists of the top layer 17 with florescent beads 19, a sensing element 11 and the portion of the bottom layer 14 that overlaps the well 23. The suspended membrane does not attach to the glass substrate 12. This base structure resembles a bridge. Only parts acting as the "bridge pier" are bonded to the glass substrate. The suspended membrane is the "bridge deck".

The base and the top polymeric membranes 14, 17 may be made of any suitable deformable polymeric material, such as PDMS. Polymer materials with good elasticity, biocompatibility, and transparency (e.g., thermoplastic polyurethane) may be used to make the base and top polymeric membranes 14, 17.

The sensing element or strain sensor 11 may be made of any material capable of measuring the cellular activities of the cardiac cells. Examples of materials that can be used in the sensing element include carbon nanotube (CNT), gold (which can be precisely patterned using conventional microfabrication means; [67]), platinum [68], carbon ink [18], graphene [69], and so forth.

Means for measuring an electrical resistance 18 of the sensing element may be connected to the sensing element(s) 11.

The device 10 may include a substrate 12, and the first side 21 of the polymeric base membrane 14 may be connected or bonded to the substrate 12. The substrate may be made of glass, however, other materials may also be used, preferably materials that are optically transparent, such as polycarbonates, polystyrene, polyvinyl chloride, polylactide, and capable of supporting the polymeric membranes without bending or substantially bending.

The polymeric base membrane 14 may include a hole 24 configured to receive a tubing means 13, and microchannels 16 connecting the well's cavity 23 with the hole 24. The microchannels may also interconnect the wells within the same device. The tubing 13 may be connected to a pumping means that can apply pneumatic pressure on the wells to bulge the suspended membrane.

The device may further include a polymeric ring 25 that can be coupled onto the portion of the top polymeric membrane 17 that forms the suspended membrane. The rings 25, which may also be made of PDMS, may be bonded onto the top surface 17 of the device array as culture chambers. The cells to be studied may be grown inside the rings.

Advantages in structure: In reference [18], the reported piezoresistive sensors are rectangular-shaped beams (cantilevers) for contractility measurement. The structure has edges that are free of constraints, so has lower rotational stiffness than that with peripheral constraints. Asymmetrical stimulation occurs due to cardiomyocyte contraction or medium perturbation, which leads to warping, thus invalidating the model used in reference [18] because the model assumes perfect pure bending. The device of the present invention is an axisymmetric structure, which is peripherally constrained (more specifically, peripherally clamped or fixed). This structure improves its resistance to asymmetrical stimulations. In addition, micro-channels are integrated into the device of the present invention; pneumatic pressure can be applied through the micro-channels to bulge the suspended membrane for mechanically stimulating cardiomyocytes (e.g., for inducing the maturation of cardiomyocytes).

Continuous Measurements of Cells

The device of the present invention may be used in methods to continuously measure cellular activities such as contractility, beating rate, beating rhythm as so forth. The device of the present invention is capable of performing continuous, long-term (1, 2, 3, 4, 5, 6, 7, 8, 9, 10, 11, 12, 13, 14, 15 days or more than 15 days) measurements of cells seeded on the portion of the top polymeric membrane that forms part of the suspended membrane. Contraction, beating rate, beating rhythm of the seeded cells on the deformable polymeric membrane induces an electrical resistance change of the strain sensor(s) of the device. As reported in the Examples below, the continuous reading of the sensor signals may be used to study through a period of time to determine, when cardiomyocytes start to beat, calculate averages contractile stress.

Among the reported piezoresistive cantilevers, $6.13\times10^{-5}$ is considered to be the threshold between low sensitivity and high sensitivity [18, 19, 65, 66]. As such, in this document, "high sensitivity" means values higher than $6.13\times10^{-5}$, and "low sensitivity" means values lower than $6.13\times10^{-5}$. The signal-to-noise ratio (S/N) of a device with this sensitivity ($6.13\times10^{-5}$) is ~3. S/N≥3 is generally considered acceptable. The device of the present invention achieved sensitivity values larger than $6.13\times10^{-5}$. In the device of the present invention, a value of $1.3\times10^{-2}$ has been achieved, which is the largest value (i.e., highest sensitivity) reported so far.

Electrical signals of the strain sensor are caused by the cyclic vertical deflections of the suspended membrane, which is induced by the contraction of cardiomyocytes cultured on the top surface of the suspended membrane. Accordingly, in one embodiment, the device of the present invention can be used to measure the functional properties (contractility, beating rate and beating rhythm) of animal cardiomyocytes including hiPSC.

The device of the present invention may also be used to study, test, or evaluate how drugs effect the seeded cells. By "drug" is broadly meant any substance, compound or composition of matter, without limitation, which is introduced into the cell culture medium to determine its effect on the cells. "Drug" also include any substance, compound or composition of matter that come into contact with a cell to determine its effect on the cell.

The present device makes it possible to perform comprehensive measurements of the cells and quantify cell responses to different concentrations of agonists and antagonists. As a result, measurements can be made in a matter of seconds or over a period of minutes, hours, or even days, so long as the viable cells can be maintained under normal culture conditions. The time course of the measurements can be readily adapted by the evaluator to provide the breadth of information needed to determine the effect of the test drug on the cells, or to provide sufficient data to permit comparisons of the effect of the drug on a variety of cell types.

The methods and apparatus of the present invention are also ideal for measuring the effect of one or more drugs in combination with another drug, or of one or more drugs in combination with one or more other substances, or of a drug administered with any other substance (carriers, adjuvants, enhancers, or the like).

Since the device of the present invention can carry an array of suspended membranes, one device may be used to study different cell types (for example, one cell type per suspended membrane) under the same conditions, or the same cell type under different conditions (for example, different drugs per suspended membrane, or same drug at different concentrations per suspended membrane).

To aid in the understanding and preparation of the within invention, the following illustrative, non-limiting, examples are provided.

Examples

1. Materials & Methods 1.1 Fabrication of Device Arrays

The device's 10 compositions are schematically shown in FIG. 1, consisting of a substrate 12, which may be made of glass, a PDMS base structure 14 including a portion 15 of the second side 22 that forms the floor 29 of the well 15 and micro-channel 16, a top PDMS layer 17 embedded with fluorescent beads 19, and CNT strips 11 sandwiched within the two PDMS layers. The CNT strips 11 are disposed over the suspended membranes 15. The base structure 14 includes a first side 21, which is the side facing the substrate 12, and a second side 22.

Figure 2B:
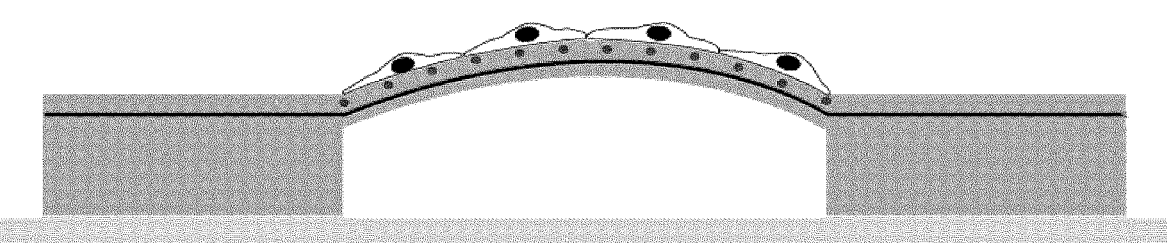
FIG. 2B is a schematic diagram illustrating membrane deflection induced by systole of monolayer human induced pluripotent cells stem cells-cardiomyocytes (hiPSC-CMs).

As shown in FIG. 2A-B, the base structure 14 includes a well or cavity 23. The floor of the cavity is formed by the second side 22 of the base structure 14. The micro-channels 16 connect the cavities 23.

Figure 6:
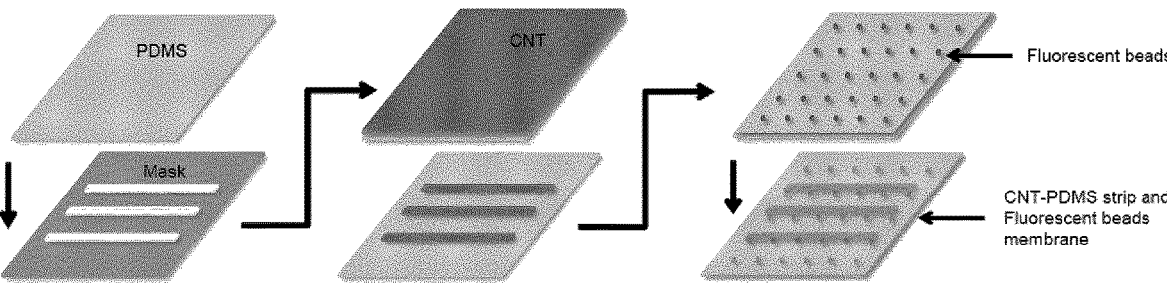
FIG. 6. Schematic showing strain sensor fabrication by screen printing thin strips of CNT on PDMS, followed by encapsulation in PDMS (formation of a composite membrane with total thickness=200 μm); spacers determine the membrane thickness and ensure accessibility of embedded CNT strips for bonding of electrodes.

Steps in fabricating the CNT-PDMS device arrays are shown in FIG. 6. PDMS (1:20 as the ratio of curing agent and PDMS polymer) was poured into a mold, baked at 80° C. for 4 hours to form 16 device arrays with each array containing 3 suspended membranes (6.35 mm in diameter and 100 μm in thickness). The baked PDMS was peeled off and cut into 16 strips, and the membranes were connected by underlying micro-channels, forming the PDMS base structure. The PDMS base structure was treated by plasma and bonded to the glass slide. A hole (diameter: 0.8 mm) was formed using a biopsy punch, and a plastic tubing was connected to the underlying channels, thereby connecting the tube to the cavities.

CNTs (diameter: 20-30 nm, length: 10-30 μm, Cheaptubes Inc. USA) and PDMS (Sylgard 184, Dow Corning) were blended with a mixing weight ratio of 1:5. CNT stripes (50 m in thickness, 300 μm in width, and 1 cm in length) were formed on the surface of the suspended membrane by screen printing. Electrical connectors were then bonded to the glass slide using partially cured PDMS and connected to the strain sensors by using additional uncured CNT-PDMS blends, which were baked for 4 hours. For verifying device membrane deflections caused by cardiomyocytes' contraction through fluorescence imaging, 1:20 PDMS mixed with fluorescent beads (mean particle size: 0.5 m; fluorescence: λex~575 nm, λem~610 nm; Sigma) was spin-coated at a speed of 600 rpm to form a thin film on the CNT-PDMS layer. This layer was termed fluorescent bead layer in FIG. 1A. The device was then oven baked at 80° C. for 4 hours.

Figure 3:
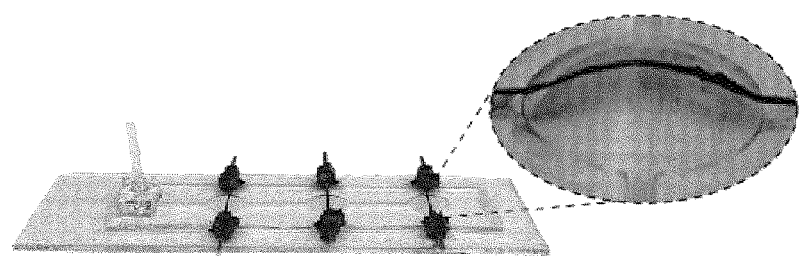
FIG. 3 is a graph of a completed device according to one embodiment of the present invention. Inset shows brightfield under 16.7 kPa.

Custom-made PDMS rings were finally bonded onto the top surface of the device array as culture chambers. FIG. 3 shows a completed device array without the PDMS rings.

1.2 Calibration of CNT-Sensors

The contractile stress of the hiPSC-CMs was determined according to Stoney's equation [31] which requires the relationship between the relative resistance change ($\Delta R/R_0$) and vertical displacement ($\Delta h$) of the membrane to be established. For device calibration, a pneumatic pressure was applied using a diaphragm pump (Schwarzer, model SP 500EC) and a programmable pressure regulator (Marsh Bellofram, model 3420). The pump delivered pressure (P) into the device channels through a single inlet to bulge the suspended membrane. The height change at the center of the membrane, $\Delta h$ was measured using a zoom system (Navitar 126, Rochester, NY), and P was controlled by a custom-made LabVIEW program. Meanwhile, a constant voltage of 2.5 V was applied to each CNT sensor, and the electrical resistance signals were collected at a sampling rate of 10 Hz using an impedance spectroscope (HF2IS, Zurich Instrument). Prior to calibration, the CNT sensors were pre-conditioned via pneumatic straining for 24 hours to ensure reproducible resistance signals. During calibration, $\Delta h$ and electrical resistance (R) were recorded under different pressures.

1.3 Finite Element Analysis

Finite element analysis (FEA) was conducted to characterize the vertical displacement and strain profile in the device membrane, using COMSOL Multiphysics (Comsol Inc., Version 5.1). The membrane had an elastic modulus of $467.5\pm10.27$ kPa (n=6), measured by AFM, and was modeled as an isotropic elastic material with Poisson's ratios of 0.49. The elastic modulus of the membrane, experimentally measured dimensions of the device structures, and applied pressure were used in FEA. In simulation, the applied stress was pressure was set to be 3.43 kPa, which was converted from the contractile stress of 4.5 kPa generated by a mono-layer of hiPSC-CMs as reported in [18]. In order to quantify the vertical membrane displacement for different membrane thicknesses (10 μm to 1,000 μm), the loop function in Comsol was employed. Strain distributions in the membrane for each thickness were also obtained in simulation.

1.4 hiPSC-CMs Culturing and Contractility Measurement

Human induced pluripotent stem cell-derived cardiomyocytes (hiPSC-CMs) were obtained from Cellular Dynamics International. Prior to culturing, all CNT-PDMS devices were UV sterilized. The sterilized CNT-PDMS device membranes were coated with matrix mixture consisting of fibronectin, gelatin, and laminin and incubated at 37° C. for at least 4 hours. Cells 26 were plated at a density of $1.56\times10^5$ cells/cm$^2$ in iCell Cardiomyocyte Plating Medium (Cellular Dynamics International) and cultured at 37° C./5% CO$_2$. Cells were thawed in hiPSC-CMs Plating Medium (Cellular Dynamics International) and centrifuged for 5 mins at 180 g. After four hours of post-plating, the plating medium was replaced with iCell Cardiomyocyte Maintenance medium, and the maintenance medium was subsequently replaced every second day. The monolayer of cells was cultured for a period of 10 days. Once after hiPSC-CMs were seeded, the device array 10 was placed in a humidified 37° C. incubator with 5% CO$_2$, and the electrical signal of the CNT sensors started to be recorded. A constant voltage of 2.5 V was applied to the CNT-PDMS sensors, and sensor signals were recorded with a sampling frequency of 10 Hz. Simulation results (FIG. 10D) show that the potential temperature rise caused by the power consumption of CNT sensors is negligible.

1.5 Immunofluorescence Staining

The hiPSC-CMs (shown as 26 in FIG. 2) cultured on the device array were stained and compared with the cells grown on the Petri-dish. The cells were fixed after culturing for one, three, five, or ten days, washed twice with PBS, and fixed in 4% formaldehyde for 15 min at room temperature. Subsequently, cells were washed three times with wash buffer (0.01% Triton X-100 in TBS), permeabilized with 0.1% Triton X-100 in TBS for 15 minutes, washed three times with wash buffer, and incubated in fresh antibody diluent solution (5% goat serum in wash buffer) for 1 hour at room temperature. The cells were incubated with primary antibodies, mouse-raised anti-α-actinin diluted at 1:500, and rabbit-raised anti-MYH7 at 1:100 (both Sigma, St. Louis, USA) in antibody diluent, overnight at 4° C., then Alexa Fluor® 594-anti-rabbit and Alexa Fluor® 594-anti-mouse secondary antibodies at 1:1000 in antibody diluent (Cell Signaling Technology, Danvers, MA) with Hoecht 33342 solution (Thermo Scientific) diluted 1:50,000, at 1 hour at room temperature, and stored in TBS prior images. Images were acquired on a spinning disk confocal microscope (DMi8, Leica, German) equipped with EM-CCD camera (C9100-13, Hamamatsu, Japan) and analyzed in ImageJ (1.8, National institutes of Health, USA).

1.6 Calcium Imaging

Cardiomyocytes' beating behavior is closely related to the influx of Ca$^{2+}$. Calcium 5 indicator (FLIPR, Molecular Devices) was employed for binding Ca$^{2+}$ ions. Specifically, hiPSC-CMs were firstly loaded with a fluo-5 Ca$^{2+}$ indicator in a medium of loading buffer (HEPES). The cells were incubated in a humidified 37° C. incubator with 5% CO$_2$. Then cells were re-washed five times with the medium. Fluorescence was excited at 488 nm and recorded at 520 nm. Fluorescence imaging was focused on the plane of cardiomyocyte beating. Fluorescence videos (resolution: 512×384 pixels) were captured by a CCD camera (Retiga Exi, Qimaging) under 20× at 20 frames per second. Ca$^{2+}$ was expressed as the intensity of fluorescence signals.

1.7 Drug Test

Five drugs (Isoproterenol, Verapamil, Omecamtiv mecarbil, Ivabradine, and E-4031) from Sigma-Aldrich were tested. Drug stocks were kept at 4° C. prior to use. Drug tests were performed on hiPSC-CM monolayers during culture days between 10 and 14. Before testing each drug, 100 μL serum-free media was added to each well of the device array, and the dose of the drug was increased gradually by adding 1 μL more drug of higher concentration each time. After each drug addition, cells were incubated for 10 hours for each dose before CNT sensor signals were recorded to reflect the drug effect. Since the effective concentrations of each drug are different, varied concentrations were used for the five drugs.

1.8 Statistical Analysis

Each set of data was from 3 to 6 experiment repeats and presented as values of the mean and the standard error of the mean. For differential analysis, all statistics of recorded data was processed using Student's t-test with levels of 0.05, 0.1 when they were compared to the control group. All data sets passed Shapiro-Wilk normality tests and equal variance tests. Fourier analysis was processed by Matlab (MathWorks Inc, USA). Microcal Origin 8.5 software (Microcal, Northampton, MA, USA) was used for statistical processing of data.

1.9 Cardiomyocyte Contractile Stress Analysis hiPSC cardiomyocytes were cultured on the PDMS membrane of the CNT-PDMS devices and formed an isotropic monolayer with no preferential alignment. The contractile stress generated by cardiomyocytes monolayer during synchronous systole was calculated from the experimentally measured data (i.e., CNT sensor's electrical resistance change). Stoney's equation [1] is commonly applied to calculate stress in a thin film coated on a substrate as a function of curvature of the bilayer [2, 3]. In the present CNT-PDMS devices, the cardiomyocyte monolayer is the thin film, and the suspended PDMS membrane acts as the substrate. Contractile stress in the isotropic cardiomyocyte monolayer is regarded as uniform stress and is uniformly exerted on the PDMS membrane. The contractile stress is $$\sigma_c = \frac{E_m t_m^2}{6C(1 - v_m)t_c} \tag{1}$$

where $E_m$ and $v_m$ are the elastic modulus and Poisson's ratio of the PDMS membrane, and C is the radius of curvature. PDMS membranes were fabricated by mixing the base and curing agents in the ratio of 20:1, resulting in an average $E_m$ value of 467±10.27 kPa (n=6) as measured by AFM. Since PDMS is considered incompressible [4], $v_m$ was set to be 0.5. The thickness of the PDMS membrane $t_m$ was measured to be 200±11 µm via optical surface profilometry. The thickness of an hiPSC-cardiomyocyte monolayer $t_c$ was measured to be 3±0.5 based on confocal imaging, and the average value 3 µm was assigned to $t_c$.

In order to quantify the radius of curvature, C in (1), the peak value of membrane vertical deflection, Δh needs to be measured in experiments. The relationship between Δh and CNT sensor's resistance change was experimentally calibrated as $$\Delta h = k\frac{\Delta R}{R_0} \tag{2}$$

where k was determined to be 322.58. According to Pythagoras's theorem, the radius of curvature C is $$C^2 = (C - \Delta h)^2 + r^2 \tag{3}$$

where r is the radius of the suspended PDMS membrane (r=6.35 mm). Substituting (2) and (3) into (1) gives the contractile stress generated by cardiomyocytes.

$$\sigma_c = \frac{E_m t_m^2}{3(1 - v_m)t_c} \times \frac{k \cdot \frac{\Delta R}{R_0}}{r^2 + \left(k \cdot \frac{\Delta R}{R_0}\right)^2} \tag{4}$$

2. Results

The use of hiPSC-CMs as vehicles for disease testing and therapy discovery is currently limited by the inability to properly measure the complex activities of the cardiac cells. We developed a platform that is capable of comprehensively measuring the beating rate, rhythm, and contractility in a monolayer of hiPSC-CMs. The CNT-PDMS device arrays are well suited for long-term cell culturing and monitor gradual changes of hiPSC-CMs contractility during the culturing process.

2.1 CNT-PDMS Device Characterization
2.1.1 Device Characterization

Figures 7A, 7B, 7C, 8A, 8B:
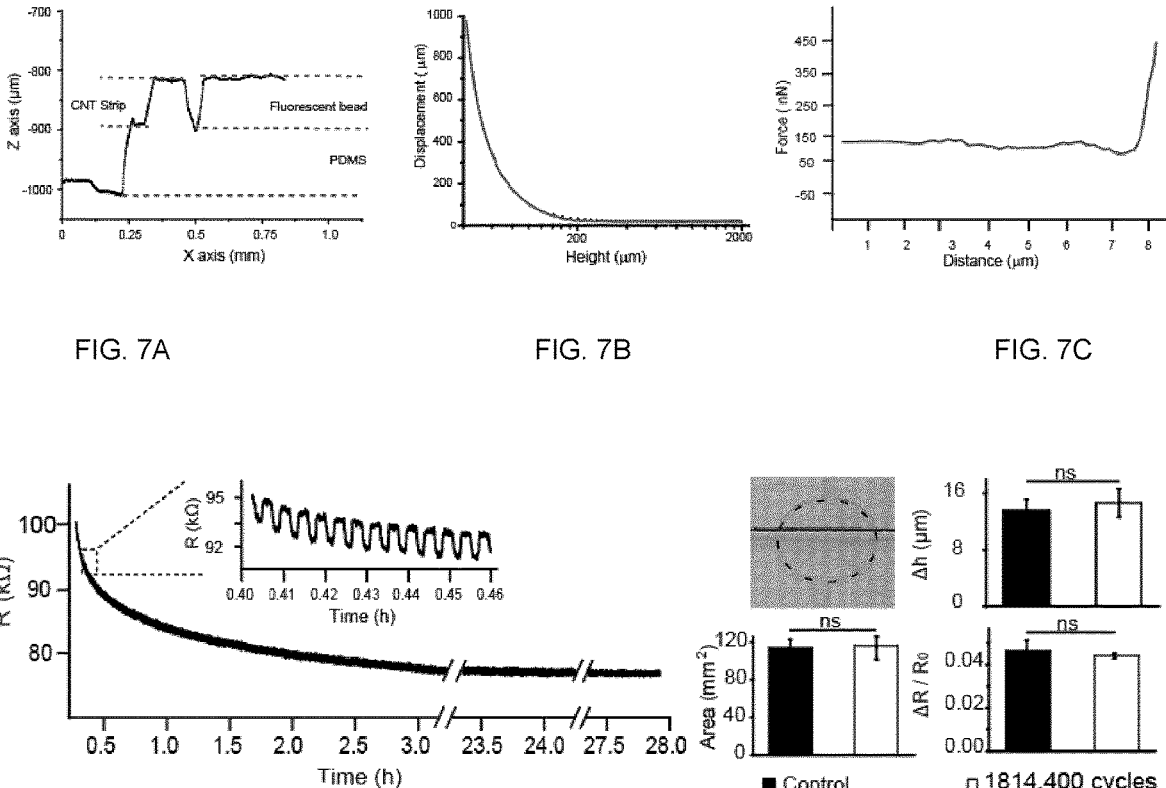
FIGS. 7A-7C: Optical step profiler shows the total thickness of PDMS membrane is 200 μm and the thickness of CNT strip is 50 μm (FIG. 7A. Finite element analysis was conducted to simulate the strain change with the thickness increment of the device suspended membrane (FIG. 7B). AFM was applied to determine the Young's Modulus of PDMS membrane (467.5±10.3 kPa, n=6) (FIG. 7C).
FIG. 8A. Device pre-conditioning.
FIG. 8B After pre-conditioning, the devices underwent fatigue testing. Membrane displacement Δh, membrane area, and $\Delta R/R_0$ before and after fatigue testing (under the actuation pressure of 3.43 kPa at 1 Hz for 21 days) did not change significantly. Measurements were made on 9 device elements/membranes.

The thickness of the suspended PDMS membrane was measured with an optical step profiler to be 200 µm (FIG. 7A). The suspended membrane has two layers of PDMS sandwiching a stripe of CNT-PDMS. The thickness and width of the CNT-PDMS stripe were 50 µm and 150 µm, respectively. During device design, FEA (FIG. 7B) showed that the vertical displacement of a 500 µm thick PDMS membrane was 14.8 µm caused by an applied stress of 4.5 kPa (contractile stress caused by a monolayer of hiPSC-CMs reported in [18]). Under the same condition, the vertical displacement of a 200 µm thick PDMS membrane was 32.17 µm. Therefore, we chose the 200 µm thickness in the final device design to achieve a relatively large membrane displacement and strain sensor's signal change $\Delta R/R_0$ (i.e., improved sensitivity). AFM indentation (FIG. 7C) was conducted and measured the elastic modulus of the suspended membrane to be 467.5 kPa.

2.1.2 Device Calibration

Figure 4:
FIG. 4 is a confocal microscopy image showing membrane budging under 16.7 kPa.

When hiPSC-CMs are cultured on the device membrane (FIGS. 2A, 2B), the cells exert compressive stress on the top surface of the PDMS membrane during synchronous contraction. [32, 33] According to the thin film model [34] and consistent with previous observations of epithelial cells' contraction [35], compressive stress causes the membrane to concave upwards, and the radius of curvature is determined by the magnitude of the stress exerted by hiPSC-CMs. To mimic the process and establish a calibrated relationship between the membrane displacement amplitude and CNT strain sensor's electrical resistance change, a pneumatic pressure was applied to bulge the suspended membrane. Inset in FIG. 3 shows membrane bulging under the applied pressure of 16.7 kPa. To accurately measure the membrane displacement amplitude, the fluorescent beads embedded in the top PDMS layer were used for confocal microscopy imaging to measure membrane displacements (FIG. 4).

To pre-condition the CNT strain sensors, a sinusoidal pneumatic pressure (4 kPa, 0.1 Hz) was applied, and the corresponding periodical change of strain sensor's resistance (R) is shown in FIG. 8A. The initial resistance value (R) ranged from 96.2 kΩ to 311.7 kΩ across devices. During pre-conditioning, the resistance change of the strain sensors decreased over time until the 24th hour.

When equilibrium was reached, the resistance values of the devices ($R_0$) varied from 68.3 kΩ to 94.4 kΩ (Table 2 lists R and $R_0$ values of nine device elements before and after pre-conditioning). In this work, the normalized quantity, $\Delta R/R_0$ was used and correlated with applied pressure (see FIG. 9A and FIG. 10C) through device calibration. The sensitivity ($\Delta R/R_0$ vs. pressure) of the nine device elements was experimentally determined to be 0.01 kPa$^{-1}$±0.0003 kPa$^{-1}$. After device pre-conditioning, fatigue test was performed to evaluate potential structural degradation of the device membrane as well as CNT strain sensor's signal stability. In the 21-day fatigue test, a sinusoidal pressure (3.43 kPa [18], 1 Hz) was applied to mimic the effect of cardiomyocyte beating on the device membrane, resulting in membrane deflections for $1.81 \times 10^6$ cycles. As the gas permeability of PDMS is approximately $1.0 \times 10^3$ Barrer [36, 37], for the applied pressure of 3.43 kPa, it would take $4.39 \times 10^7$s to completely leak the compressed air through the PDMS membrane. Thus, considering the time scale of the applied pressure (1 Hz), air leakage was negligible. The same pre-conditioning process and fatigue tests were conducted on three independent device arrays (totally 9 device elements/membranes). Before and after the fatigue tests, we measured the vertical displacement ($\Delta h$) at the center of the membrane, the area of membrane ($S$), and the relative resistance change $\Delta R/R_0$ of the CNT sensor for each of the tested 9 device elements/membranes. These three parameters' respective values before and after fatigue testing are $13.58\pm1.59$ $\mu m$ vs. $14.67\pm2.02$ $\mu m$, $113.43\pm0.77$ $\mu m^2$ vs. $116.08\pm0.38$ $\mu m^2$, and $(4.64\pm0.73)\times10^{-2}$ vs. $(4.22\pm0.98)\times10^{-2}$ (FIG. 8B). The p values in all three cases were larger than 0.1. These results indicated no significant membrane fatigue or CNT strain sensor signal degradation after 21 days of periodic straining.

Figures 9A, 9B, 9C, 10A, 10B, 10C, 10D:
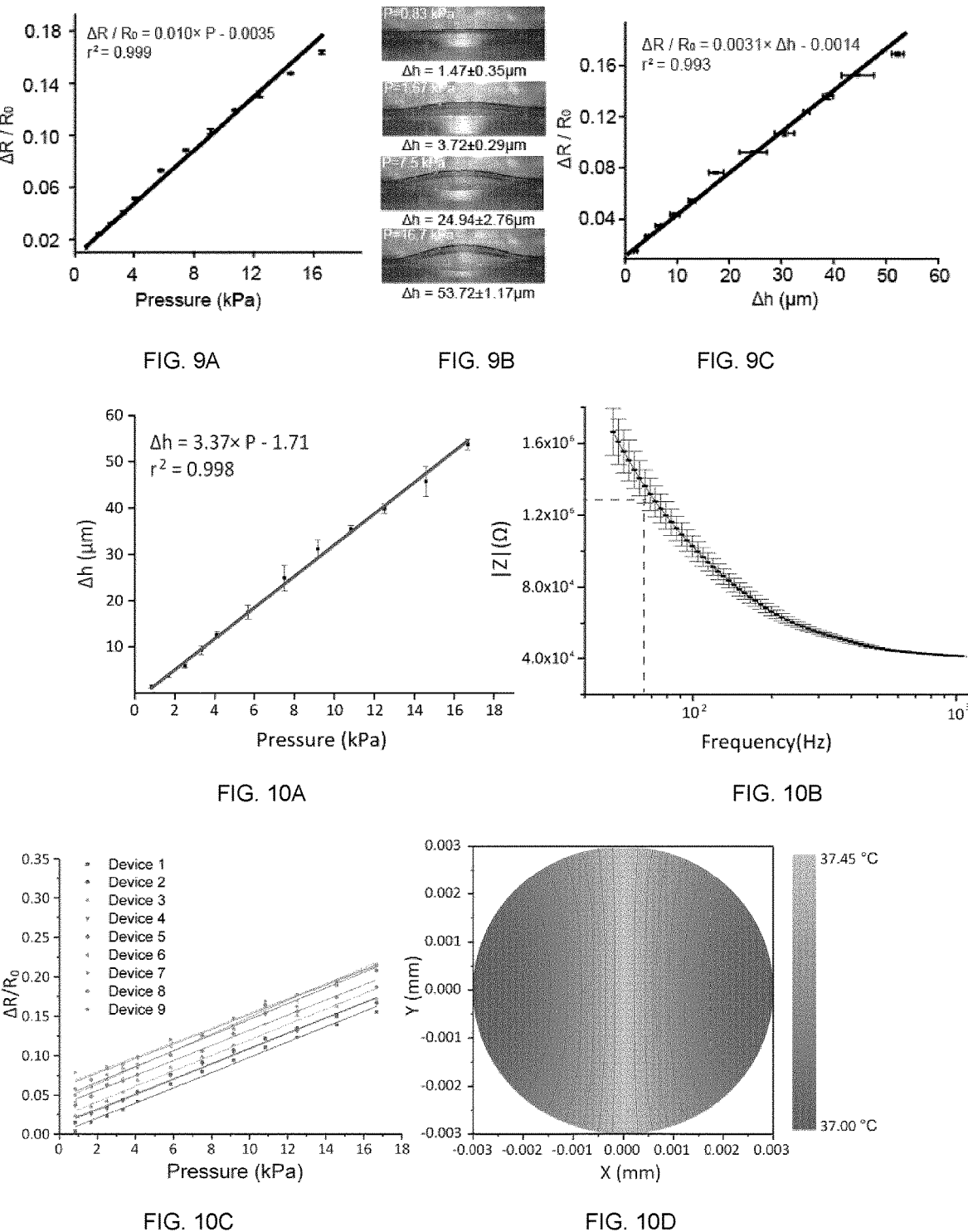
FIG. 9A is a graph illustrating the calibrated relationship between resistance change ($\Delta R/R_0$) at different applied pressures.
FIG. 9B are optical microscopy images of membrane deflections under different actuation pressures.
FIG. 9C is a graph illustrating calibrated relationship between $\Delta R/R_0$ and maximal vertical displacement (Δh) of the device membrane.
FIGS. 10A to 10D. Supplementary characterization of CNT-PDMS device. (A) Experimentally calibrated relationship between membrane deflection and applied pressure. (B) Frequency response of CNT-PDMS device: the frequency was scanned from 1 Hz to 1 kHz, the red dash line was half-power point. (C) Calibrated relationship between resistance change ($\Delta R/R_0$) and applied pressure. The nine device elements shown in this figure overall have a sensitivity ($\Delta R/R_0$ vs. pressure) of 0.01 kPa$^{-1}$ 0.0003 kPa$^{-1}$. (D) Finite element simulation results show that with 0.083 mW for a continuous 48 hours, the very central region of the membrane, where the CNT stripe is located, has a temperature rise from 37° C. to 37.45° C. It has been reported that temperatures higher than 38° C. can induce a noticeable fluctuation of cardiomyocytes' beating rate and causes dysrhythmia contractions. [25]

We then calibrated the relationship the relative resistance change ($\Delta R/R_0$) of the CNT strain sensor and the vertical displacement ($\Delta h$) of the membrane. A pneumatic pressure ranging from 0 kPa to 16.7 kPa was applied to bulge the suspended PDMS membrane. $\Delta h$ was measured by microscopy imaging (FIG. 9B), and the CNT resistance signal was simultaneously recorded by impedance spectroscopy. FIG. 10 summarizes the calibrated membrane displacement under different actuation pressures, resulting in $\Delta h=3.37\times P-1.71$ ($r^2=0.998$). The relationship between $\Delta R/R_0$, and P was also calibrated, resulting in $\Delta R/R_0=(0.010\pm0.0003)\times P-0.0035$, ($r^2$: 0.999, n=9 device elements), as shown in FIG. 9A. From these calibration results, $\Delta R/R_0$ and $\Delta h$ were quantitatively related, $\Delta R/R_0=0.0031\times\Delta h-0.0014$ ($r^2=0.993$). When hiPSC-CMs were seeded on the device membrane, the cell-generated contractile stress was determined with these calibrated relationships.

2.2 Measurement of hiPSC-CMs' Physiological Structures

Figure 12:
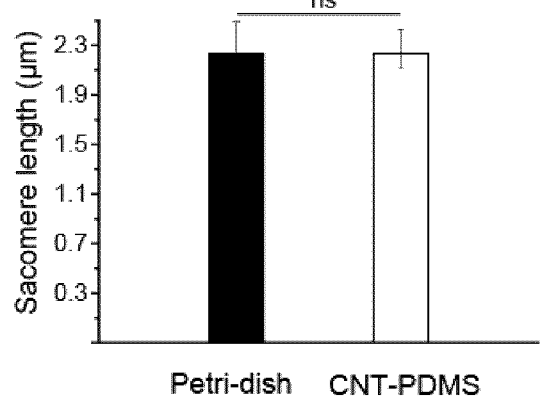
FIG. 12 is a graph illustrating the average sarcomere length of hiPSC-CMs cultured on a Petri dish (black bar; 2.25±0.19 μm, n=70) and on a device according to one embodiment of the present invention (white bar; 2.16±0.13 μm, n=70), measured on day 10.
Figure 13:
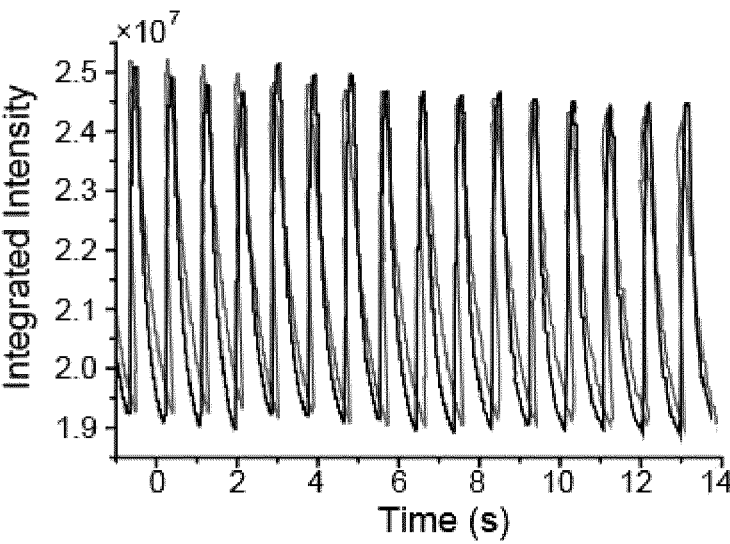
FIG. 13 is a graph illustrating calcium transient. Calcium transient was evaluated by the fluorescence intensity of calcium indicator fluo-5 in calcium imaging. Spontaneous calcium transients indicate that cells were electrically coupled on PDMS-CNT devices. The durations of calcium release were 0.85±0.09s on PDM-CNT devices (black line) and 0.87±0.04 s on Petri-dish (grey line).
Figures 18A, 18B:
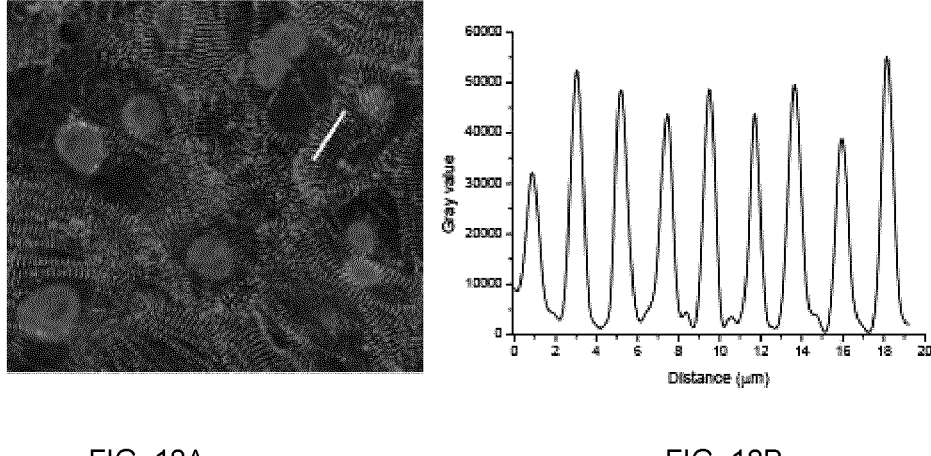
FIG. 18A is a fluorescence image of a sample of hiPSC-CMs cultured on the CNT-PDMS device according to one embodiment.
FIG. 18B is a representative line-scan profiles for the fluorescence images were shown to demonstrate the variation of gray value for α-actinin marker along the myofibrils. The x- and y-axes signify the length of the sarcomere and the gray value (arbitrary units), respectively.

The CNT-PDMS devices were UV sterilized, and the sterilized CNT-PDMS device membranes were coated with matrix mixture consisting of fibronectin, gelatin, and laminin. To assess the structure of the force-generating unit (sarcomere) and physiological features of the hiPSC-CMs grown on the CNT-PDMS device, $\alpha$-actinin staining and calcium imaging were conducted. The protein, $\alpha$-actinin is necessary for the attachment of actin filaments to the Z-lines in cardiomyocytes. Immunostaining images of hiPSC-CMs grown on the PDMS-CNT device and in Petri-dish were compared. FIGS. 11A and 11B show that $\alpha$-actinin of the two groups both cross-linked to actin filaments and both displayed evenly striated fibers. Sarcomere length is an indicator of the degree of overlap between the thick and thin filaments within the actin-myosin contractile apparatus of cardiomyocytes. A longer sarcomere length indicates that cardiomyocytes are capable of forming a larger sliding distance between the actin and myosin filaments, resulting in a higher degree of overlap and larger contractile force. The sarcomere length was determined by measuring the difference of gray value in neighboring $\alpha$-actinins, as shown in FIGS. 18A and 18B. FIG. 12 shows that the measured sarcomere lengths in hiPSC-CMs cultured on the CNT-PDMS device and in Petri-dish were $2.25\pm0.19$ $\mu m$ (n=70 cells) vs. $2.16\pm0.13$ $\mu m$ (n=70 cells) (p>0.1). These results indicate the hiPSC-CMs cultured on the device membranes (Young's modulus: $467.5\pm10.27$ kPa) and those cultured in Petri dishes likely generate comparable contractile forces.

Another essential feature of cardiomyocyte physiology is the ability to rapidly increase the cytosolic $Ca^{2+}$ concentration in response to spontaneous or stimulated membrane depolarization. Experimental data (FIG. 13) shows that the integrated intensity of calcium released from the contracting hiPSC-CMs cultured on CNT-PDMS device was $2.48\times10^7\pm6.27\times10^5$, and the value of the cells cultured on petri-dish was $2.51\times10^7\pm4.91\times10^5$. In addition, the durations of calcium release were also similar ($0.85\pm0.09$ s vs. $0.87\pm0.04$ s, n=7 wells, P>0.1). The results confirmed that hiPSC-CMs cultured on the CNT-PDMS devices well preserved cardiac contractility.

2.3 Monitoring Spontaneous Contractile Behaviors of hiPSC-CMs

Figure 19:
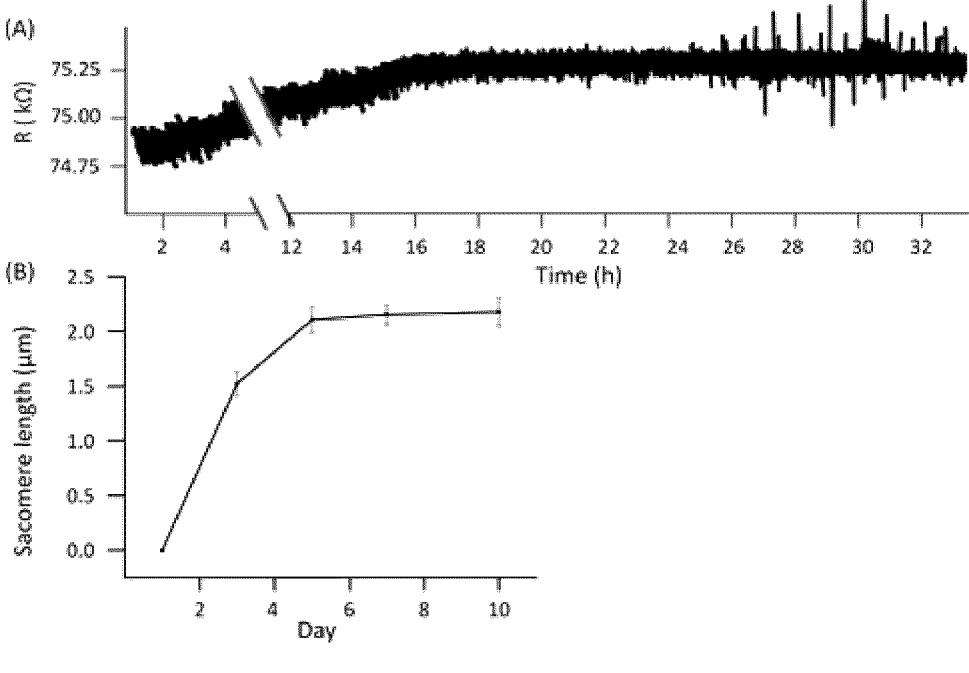
FIG. 19 (A) CNT sensor signals in the first 32 hours of cell culturing. (B) Sarcomere length development from Day 1 to Day 10.

Once after cell seeding, the device array was placed into an incubator and was connected to the impedance spectroscope, through a port on the back of the incubator, for recording the sensor signals. FIG. 19A shows the dynamic sensor signal change within the first 32 hours. It can be seen that the CNT sensor's resistance increased from 74.78 k$\Omega$ to 75.16 k$\Omega$ after 16 hours and then fluctuated around the baseline value of 75.16 k$\Omega$. The increase of the sensor signal in the first 16 hours likely reflects the cell adhesion dynamics. FIG. 19 also clearly shows the chaos state between 24 and 32 hours. It is known that cells need time (typically a few hours) to have their gap junctions completely assembled [38] during the chaos state. Therefore, those cells that started to beat cannot transfer signals to their neighboring cells.

Figure 14:
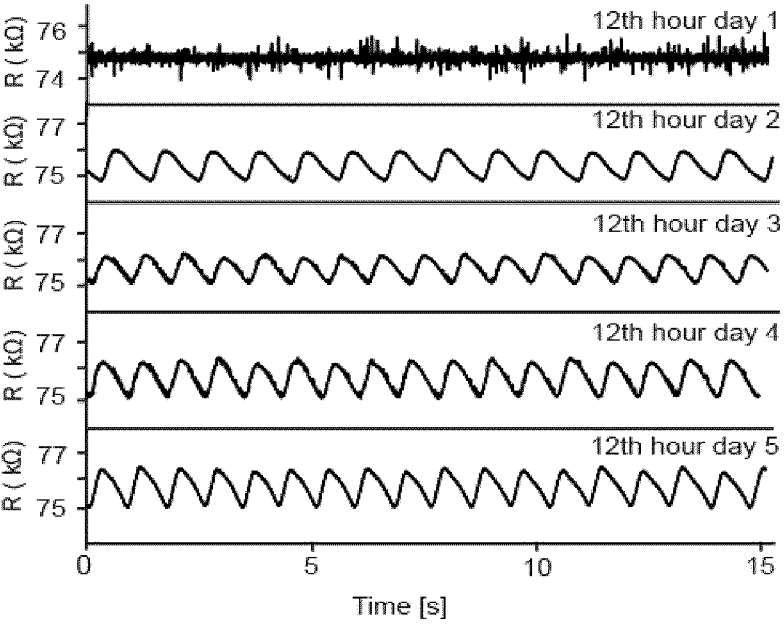
FIG. 14 is a graph illustrating recording of CNT resistance signals from day 1 to day 5 over a ten-day culturing of cardiomyocytes.
Figure 15:
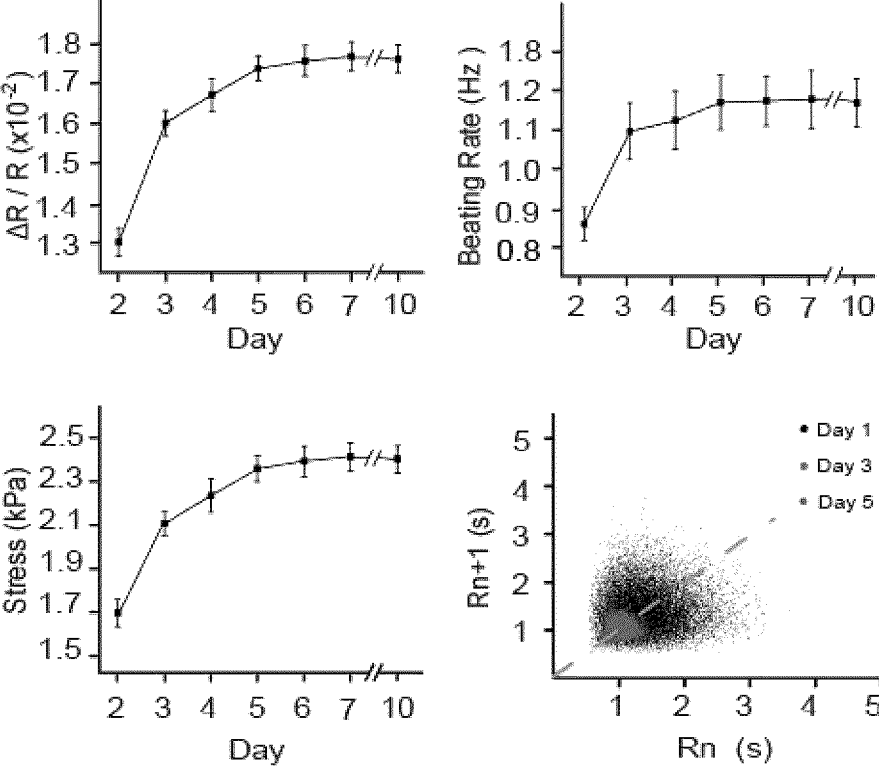
FIG. 15 are graphs illustrating measurement of cardiomyocytes over a ten-day culturing process of $\Delta R/R_0$ (top left), beating rate (top right), contractile stress evolution (bottom left). Poincare plot showing beating rhythm on Day 1, Day 3, and Day 5 (bottom right).
Figure 16:
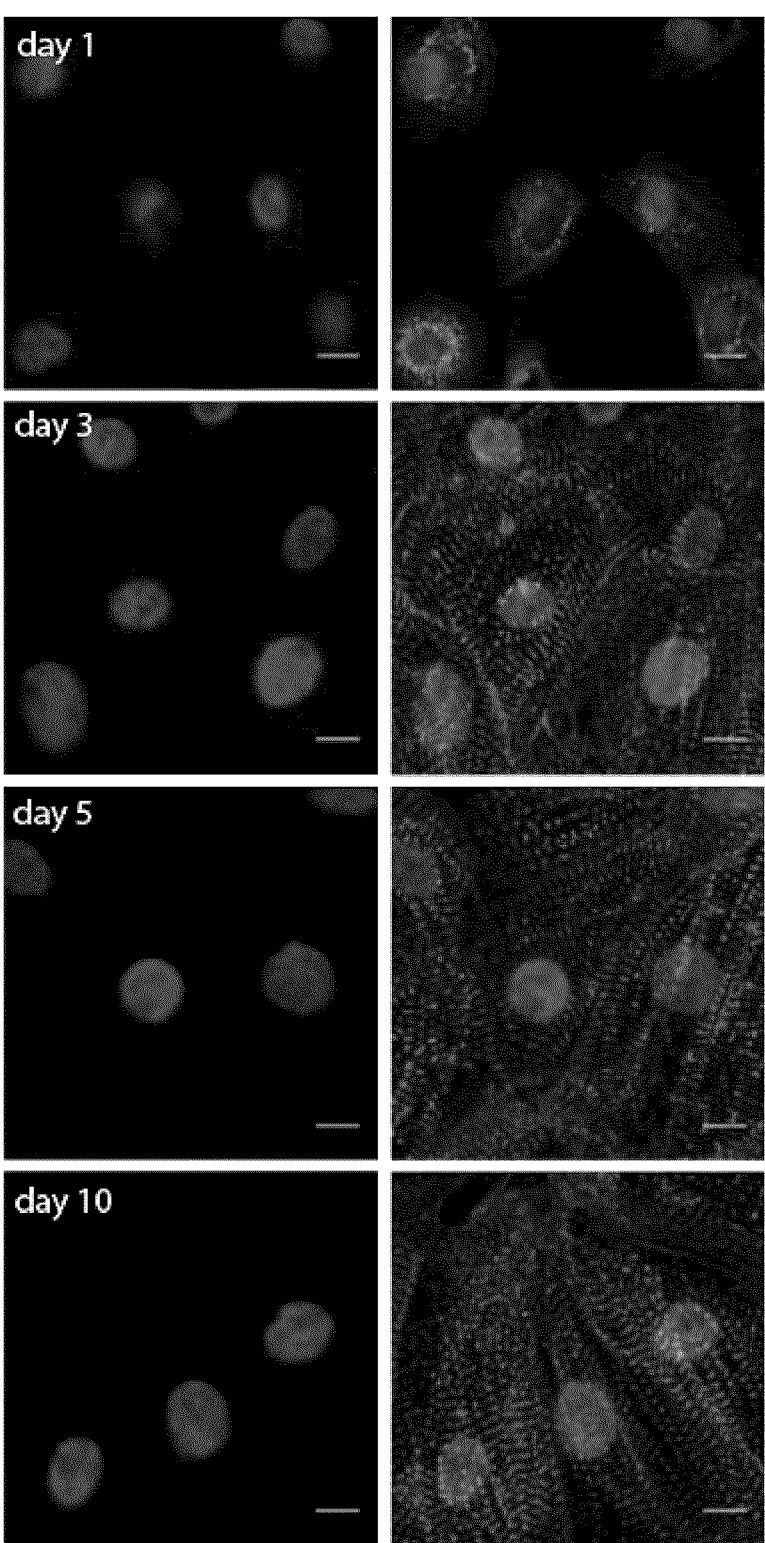
FIG. 16 illustrates α-actinin and nuclei in fluorescence images showing the development of sarcomeres at days (from top to bottom) 1, 3, 5 and 10. Scale bar: 10 μm.

FIG. 14 shows CNT sensor signals from Day 1 to Day 5 (the 12th hour on each day). From day 2, regular beating of the monolayer of hiPSC-CMs began, and the beating rate and contractile stress started to increase from Day 2. The sensor signal, $\Delta R/R_0$ (FIG. 15, top left) induced by cell beating increased from $1.30\times10^{-2}\pm3.50\times10^{-4}$ on Day 2 to $1.77\times10^{-2}\pm3.68\times10^{-4}$ on Day 5 and remained largely unchanged by Day 10 ($1.76\times10^{-2}\pm3.52\times10^{-4}$). Correspondingly, the beating rate (FIG. 15, top right) of the cells increased from $0.833\pm0.046$ Hz on Day 2 and plateaued at $1.17\pm0.068$ Hz on Day 5. The contractile stress (FIG. 15, bottom left) increased from $1.73\pm0.047$ kPa on Day 2 to $2.35\pm0.038$ kPa on Day 5 and remained largely unchanged afterwards ($2.34\pm0.041$ kPa on Day 10).

The Poincare plot (FIG. 15, bottom right), decomposed from the CNT sensor signals, reveals the beating rhythm of the cells. The beating rhythm of cardiomyocytes describes the variation of time interval between two adjacent beating periods, which can be quantitatively expressed by scatter plots known as the Poincare plot. [39] FIG. 15, bottom right, shows that the distribution of scattered points on Day 1 was scattered and covering a large area, indicating that cell beating was largely random. The covered area of the scattered plots decreased gradually, as shown by the red (Day 3) and blue (Day 5) clouds in FIG. 15, bottom right, indicating that the cells' beating rhythm became more regular.

In order to understand the contractile stress increase over the culturing period, hiPSC-CMs were fixed at the end of Day 1, Day 3, Day 5, and Day 10 and measured by confocal imaging where $\alpha$-actinin was stained in green and nuclei were stained in blue. On Day 1, immunocytochemical staining revealed that hiPSC-CMs had a small, rounded shape, there was no clear striped pattern ($\alpha$-actinin) and sarcomeres were sparse. On Day 3, cells became more elongated and exhibited clear striped patterns with a sarcomere length of $1.52\pm0.11$ $\mu m$. By Day 5, cells displayed an organized sarcomeric structure (length: $2.14\pm0.09$ $\mu m$). Compared to Day 5, cells on Day 10 had a slight but insignificant increase in sarcomere length ($2.14\pm0.09$ $\mu m$ vs. $2.16\pm0.13$ $\mu m$, P>0.1). FIG. 19B summarizes the sarcomere length development over the culturing process.

2.4 Drug Evaluation

We then applied the CNT-PDMS devices to measuring the effect of cardiac drugs. At the molecular level, cardiac contraction follows a mechanism known as excitation-contraction coupling, which involves the formation of the action potential, calcium-induced calcium release, and the formation of actin-myosin cross bridges. [40] In this work, five typical clinical drugs, which are known to affect cardiomyocytes' beating behaviors by regulating the excitation-contraction coupling process, were tested to demonstrate the device's effectiveness for quantitating the drug effects (FIG. 17A-E). Isoproterenol, Verapamil, Omecamtiv mecarbil, Ivabradine, and E-4031, respectively, act on the β-adrenergic receptor, L-type calcium channel, myosin filament, funny channel, and hERG channel, and they affect cardiomyocytes' functions by regulating contractility, beating rate, and beating rhythm.

Isoproterenol is a β-adrenergic receptor agonist. It can activate the β-adrenergic pathway, stimulate L-type calcium channels and ryanodine receptors (RyR2) on sarcoplasmic reticulum, and further cause significant increase of intracellular $Ca^{2+}$ concentration [41]. $Ca^{2+}$ binds to troponin, activates actin and myosin combination, and initiates sarcomere shortening (see solid black line in FIG. 17G). As a result, Isoproterenol is known to be able to increase both contractility and beating rate of cardiomyocytes in a dose-dependent manner. In our experiments, four isoproterenol concentrations (0.25 µM, 0.50 µM, 1.00 µM, and 2.00 µM) were tested. Each drug concentration was tested in three independent wells of hiPSC-CMs. As shown in FIG. 17A, for the 2.00 µM isoproterenol group of hiPSC-CMs, compared to the control group, $\Delta R/R_0$ increased from $1.76 \times 10^{-2} \pm 7.26 \times 10^{-4}$ to $2.98 \times 10^{-2} \pm 3.97 \times 10^3$. Contractile stress increased by 69.4% (2.34±0.093 kPa vs. 3.963±0.532 kPa), and the beating rate increased from 1.17±0.068 Hz to 1.33±0.081 Hz (n=3 and p<0.05).

When cardiomyocytes are depolarized by an action potential, $Ca^{2+}$ enters the cell through L-type calcium channel and then triggers inner $Ca^{2+}$ release from sarcoplasmic reticulum (SR), resulting in an increase of $Ca^{2+}$ concentration in *mycoplasma*, a process known as "calcium-induced calcium release" [40]. Verapamil is an L-type calcium channel (LTTC, see FIG. 17G) blocker that can decrease force generation and beating rate by inhibiting $Ca^{2+}$ transit [42]. It has been used in the treatment of cardiovascular diseases such as hypertension and cardiac arrhythmia. Our CNT-PDMS devices quantitatively revealed the drug's effect in altering the contractile stress and beating rate of hiPSC-CM monolayers grown on the suspended membranes. The four Verapamil concentrations tested in this work were 0.05 µM, 0.10 µM, 0.15 µM, and 0.20 µM, and each drug concentration was tested in three independent wells of hiPSC-CMs. FIG. 17B shows that the treatment of hiPSC-CMs with 0.20 µM Verapamil reduced the cells' beating rate by 54.5%, from 1.12±0.047 Hz to 0.51±0.069 Hz. $\Delta R/R_0$ decreased from $1.76 \times 10^{-2} \pm 7.27 \times 10^{-4}$ to $8.72 \times 10^{-3} \pm 9.85 \times 10^{-4}$, and the corresponding contractile stress decreased by 50.9% from $2.34 \pm 9.31 \times 10^{-2}$ kPa to $1.15 \pm 1.31 \times 10^{-1}$ kPa (n=3, p<0.05). In FIG. 17F, the enlargement of the cloud size corresponding to Verapamil describes increased variability of beating rate, whereas the shift of the cloud to the upper right corner of the plot indicates a decrease of beating rate.

Omecamtiv mecarbil (OM) is a new drug that specifically targets cardiac myosin to enhance effective actin myosin cross-bridge formation (see actin myosin cross-bridge in FIG. 17G). It can activate myocardial ATPase and improve energy efficiency without affecting intracellular calcium transient or level of cyclic adenosine monophosphate (cAMP). [43] Therefore, OM is able to promote contractility without increasing oxygen consumption and cardiac beating. In our experiments, four concentrations (5 nM, 10 nM, 15 nM, 20 nM) of OM were applied consecutively, and each drug concentration was tested in three independent wells of hiPSC-CMs. FIG. 17C shows that 20 nM of OM caused the amplitude of $\Delta R/R_0$ to increase from $1.69 \times 10^{-2} \pm 8.46 \times 10^{-4}$ to $2.98 \times 10^{-2} \pm 2.97 \times 10^{-3}$ (n=3, p<0.05), and caused contractile stress to increase by 76% from 2.25±0.11 kPa to 3.96±0.40 kPa (n=3, p<0.05). However, compared with the control group, 20 nM OM only slightly increased beating rate from 1.11±0.25 Hz to 1.13±0.31 Hz (n=3, p>0.1).

Funny current $(I_f)$ is an inward current that activates cardiomyocytes in the hyperpolarized membrane potential phase. It plays a role in the pace-making generation and involves the formation of the spontaneous beating of hiPS-CMs. [44] Ivabradine selectively binds to the funny-channel (see $I_f$ in FIG. 17G) and inhibits the pacemaker $I_f$ current, reducing cardiac pacemaker activity and slowing the cardiac beating without loss of contractility [44]. As shown in FIG. 17D, Ivabradine (0.10 µM, 1.00 µM, 5.00 µM and 10.00 µM) in our experiments led to a dose-dependent decrease of hiPSC-CMs' beating rate from 1.16±0.32 Hz to 0.81±0.30 Hz (n=3, p<0.05) for the concentration of 10.00 µM. Poincare plot (FIG. 17F) shows that the Ivabradine cloud is located further to the top right compared with the control group, also indicating a lower beating rate. However, contractile stress only changed from 2.26±0.43 kPa to 2.00±0.68 kPa (n=3, p>0.1) under 10.00 µM Ivabradine.

The hERG channel is a $K^+$ channel that forms $I_{Kr}$ current to conduct $K^+ \times$ out of cardiomyocyte membrane during the repolarizing phase of cardiac action potential. E-4031 is an inhibitor of the hERG channel that affects action potential by Inhibiting $I_{Kr}$ (see $K^+$ channel in FIG. 17G) [45]. As shown in FIG. 17E, E-4031 insignificantly reduced hiPSC-CMs' contractile stress from 2.47±0.48 kPa (concentration: 0.10 µM) to 2.39±1.38 kPa (concentration: 0.60 µM) (n=3, p>0.1). With the application of 0.10 µM and 0.20 µM of E-4031, hiPSC-CMs exhibited two spikes of beating rates. The arrhythmic beating occurred because E-4031 induces early afterdepolarizations (EADs), a two-step relaxation pattern in action potential. [46] Furthermore, in the presence of 0.60 µM E-4031, CNT resistance signals showed irregular pulsing patterns, which was in accordance with the random beating rates in the Fourier analysis and the extremely large cloud area of E-4031 in the Poincare plot (FIG. 17F).

DISCUSSION

Strain sensors based on CNT-PDMS have been reported. [47, 48] The device of the present invention represents the first CNT-PDMS platform for sensing contractility generated by cardiomyocytes. In the present device design, a number of considerations were accounted for. For instance, a CNT stripe was sandwiched between two PDMS layers to avoid direct CNT-cell contact and potential toxicity [49]. Furthermore, it is known that substrate stiffness can affect cellular physiology [50, 51]. On substrates that have a stiffness lower than 400 kPa, sarcomere length and its shortening velocity of cardiomyocytes have been shown to significantly decrease [51, 52]. Since too high a substrate stiffness leads to a poor device sensitivity for measuring cardiomyocytes' contractility, in this work, we used a PDMS mixing ratio of 1:20 which resulted in a substrate stiffness of 467.5±10.27 kPa. With this substrate stiffness, cardiomyocytes nicely formed a monolayer with spontaneous contractility, and their sarcomere length was comparable to the cardiomyocytes grown on Petri dishes (2.25±0.19 µm vs. 2.16±0.13 µm). Meanwhile, the CNT-PDMS devices were sufficiently sensitive to detect subtle contractility variations of cardiomyocytes (e.g., caused by 5 nM Omecamtive mecarbil treatment).

The CNT-PDMS device arrays of the present invention were first preconditioned by undergoing 24 hours of periodic straining, after which the strain sensor signals reached equilibrium. Fatigue test was then performed to ensure reliable device performance throughout the cell culturing period of 14 days. In fatigue testing, dynamic pressure was applied for 21 days ($1.81 \times 10^6$ cycles) to mimic the effect of cardiomyocyte beating on the suspended membrane. The results revealed that there was no significant difference in $\Delta R/R_0$ and the elastic behavior of the membrane before and after fatigue testing. Based on the experimentally calibrated relationship between $\Delta R/R_0$ and input pressure, the sensitivity of the device was determined to be 0.01 (kPa$^{-1}$). Based on the frequency response of the device, the bandwidth was determined to be 40 Hz (FIG. 10B), which is sufficient to fully capture the contractile behaviors of cardiomyocytes (1 Hz-2 Hz).

Figure 5:
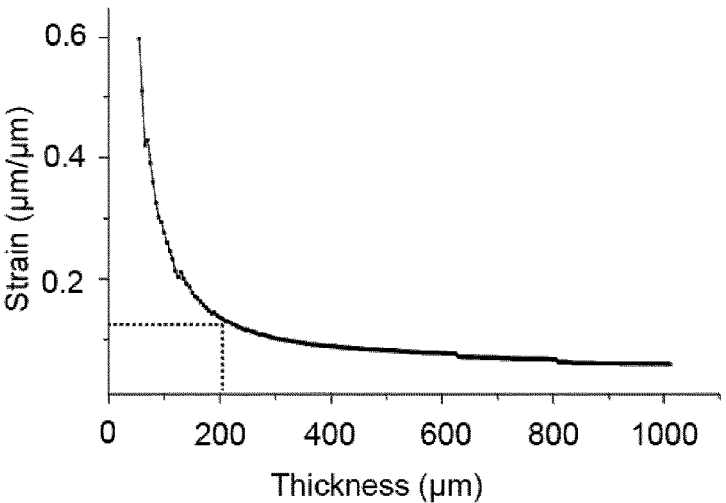
FIG. 5 is a graph illustrating simulation results of membrane maximal strain vs. different membrane thicknesses under the bulging pressure of 3.43 kPa. For PDMS membrane of 200 μm in thickness, strain is 0.14.

AFM, TFFB, micro-cantilever, and cell drum are the current methods for measuring contractile stress of cardiomyocytes. Among these methods, AFM and TFFB perform measurements on single cardiomyocytes. However, no cell is in isolation, and investigations of a single cardiomyocyte overlook the contributions of cell-to-cell communications. Cantilever and cell drum are capable of measuring contractile stress of monolayer cardiomyocytes. The reported value of contractile stress measured by cantilevers was 2-5 kPa (3.78±2.09 kPa) [53]. Since the cantilever method typically requires laser for measuring cantilever deflections, laser-induced heat could alter the contractile behavior of cardiomyocytes. The reported contractile stress value measured by cell drum was 43.1±7.5 kPa [20, 23]. Compared to the contractile stress values measured by cantilevers and cell drum, the results from our device showed that the beating of hiPSC-CM monolayers started on day 2, plateaued on day 5, and generated an average contractile stress of 2.34±0.041 kPa. This value of contractile stress is in agreement with that from cantilever measurements, but is significantly lower than the value measured by cell drum. In cell drum, the small pressure variations (<1 Pa) caused by the contraction of cardiomyocytes is challenging to be detected by the integrated pressure sensor, leading to a low signal to noise ratio (S/N) of −9.54 dB [23]. In comparison, the S/N of our device, which was experimentally determined to be 15.56 dB, is significantly higher. Furthermore, we used FEA to confirm whether yield strain occurred on our device. Yield strain determines the limits of sensing performance for CNT-PDMS device, since it represents the upper limit of contractile stress that can be applied without permanent deformation [54]. The yield strain for PDMS was varied from 0.35 to 0.55 [55]. For the present device, the simulated strain was 0.14 when the device membrane was bulged by the contractile stress of the cells generated on Day 10 (FIG. 5). It revealed that the device deformed elastically under the contractile stress generated by a monolayer of hiPSC-CMs.

Recently, device arrays integrated with electrical strain sensors were reported [18]. The strain sensors in the 3D-printed devices were formed by thermoplastic polyurethane mixed with carbon black nanoparticles. These piezoresistive cantilevers were demonstrated to be capable of measuring contractility of cardiomyocytes by continuously monitoring electrical resistance change inside a controlled incubator environment. When a monolayer of hiPSC-CMs cultured on the piezoresistive cantilevers [18] and on the CNT-PDMS devices of the present invention, the contraction of hiPSC-CMs produced an electrical resistance change ($\Delta R/R_0$) of $\sim1.7 \times 10^{-4}$ on the piezoresistive cantilevers (see FIG. 3 in [18]) vs.$\sim1.8 \times 10^{-2}$ on the devices of the present invention.

Drugs testing confirmed that our PDMS-CNT devices are capable to measuring drug effects on cardiomyocytes. Five types of drugs were tested, each with four different concentrations. Drug-induced changes in contractile stress, beating rate, and beating rhythm of hiPSC-CM monolayers were measured. Isoproterenol and verapamil are two isotropic drugs. In previous reports, isoproterenol was tested by cell drum [22], micropost [24], AFM [56], cantilever [11, 12], and TFFB [57], and were used to conduct measurements on single cardiomyocyte. At the concentration of 0.1 μM-10 μM of these two drugs, the contractile stress of a single cardiomyocyte increased by 6%-48.9% and the beating rate increased by 16.7%-20%. [24, 56, 58] Response of monolayer cardiomyocytes to these two drugs was measured by the cantilever method. Under the concentration of $10^{-3}$ μM-1 μM, the increase of contractile stress was measured to be 2%-77%, and the increased beating rates were by 15%-20% [22, 59]. Different from these studies that measured neonatal rat cardiomyocytes for drug testing, in our work, hiPSC-CMs were treated with concentrations of 0.25 μM, 0.50 μM, 1.00 μM, and 2.00 μM of isoproterenol. When the drug concentration reached 2.00 μM, the contractile stress and beating rate increased by 69.4% and 13.6%, respectively.

For verapamil testing, cell drum, cantilever and TFFB were previously used. [22, 59, 60] At concentrations of 0.05 μM-1 μM, the beating rate decreased by 23%-80% and the contractile stress decreased by 19%-61%. These measurements were made for a very short period of time and failed to monitor dynamic drug effects. For instance, TFFB only recorded cell behaviors for 15 seconds after the addition of verapamil [46]. In contrast, our device achieved continuously measurement of drug effects by capturing multiple parameters (contractile stress, beating rate, and beating rhythm). After 10 hours of recording under 0.20 μM of verapamil, our device generated a Poincare plot. Over the 10-hr period, the cloud size of the Poincare plot became larger (blue scatter in FIG. 17F), reflecting the side effect of verapamil (heart arrhythmia). This effect cannot be reflected from other existing methods due to their inability to continuously measure contractile behaviors of cardiomyocytes.

Omecamtiv mecarbil (OM) and Ivabradine regulate either contractile stress or beating rate of cardiomyocytes, but not both. OM is a new drug that is able to promote contractility without increasing cardiac beating rate. Only TFFB has been used to measure the contractile response of a single hiPSC-CM with 0.1 μM of OM [61]. Contractility generated by a single cardiomyocyte increased by 16.7% [61]. In comparison, the contractile stress of hiPSC-CM monolayers measured by our devices increased by 76% (2.25±0.11 kPa vs. 3.96±0.40 kPa) at the drug concentration of 0.02 μM. The difference can be due to the different physiological states of hiPSC-CMs. For instance, the beating rate of hiPSC-CMs used in [61] was 0.64 Hz (vs. 1.17 Hz of hiPSC-CMs used in our work), and the average length of sarcomere in [61] was 1.85 μm (vs. 2.25 μm of hiPSC-CMs used in our work). A monolayer of hiPSC-CMs contains less than 1% pacemaker-like cardiomyocytes, which are responsible for synchronous beating of the entire monolayer [62]. Ivabradine inhibits funny current ($I_f$) of pacemaker-like cardiomyocytes and reduces the beating rate of hiPSC-CM monolayers. The effect of Ivabradine has been tested by patch clamp and microelectrode array [63]. Patch clamp and microelectrode array were used to analyze beating rate through monitoring electrical impulses of cardiomyocytes under different concentrations of ivabradine [63] but are unable to measure contractile stress. The present data shows that 10.00 µM ivabradine significantly reduced the beating rate of hiPSC-CM monolayers from 1.16±0.32 Hz to 0.81±0.30 Hz but did not significantly alter their contractile stress (2.26±0.43 kPa vs. 2.00±0.68 kPa).

E-4031 is an antiarrhythmic agent. The effect of E-4031 on cardiomyocytes has been measured by patch clamp [64], which revealed that the duration of field potential was prolonged for the concentrations of 1-30 nM, and early after depolarization spikes appeared on field potential curves and caused cardiac arrhythmia at higher concentrations. The effect of E-4031 on contractile behaviors of cardiomyocytes was measured by TFFB [46] and cantilever [60]. Neonatal rat cardiomyocytes were measured for drug concentrations of 5 nM to 50 nM, and the results showed that the beating rate decreased by 30%-51%, and arrhythmic beating did not occur [60]. In comparison, our CNT-PDMS devices were capable of revealing large variations of contractile stress, random spikes of beating rate, and large cloud area in Poincare plot under the treatment of E-4031 (FIGS. 17E and 17F). The present data showed a high concentration of E-4031 (>0.6 µM) caused arrhythmic beating of hiPS-CMs, indicating cardiotoxicity of E-4031 at high concentrations.

CONCLUSION

The present invention discloses a platform that is capable of performing continuous, long-term (14 days or even more) measurement of contractility, beating rate, and beating rhythm in a monolayer of human induced pluripotent stem cell-derived cardiomyocytes (hiPS-CMs). A person skilled in the art would understand that the device of the present invention may also be used to study other cell types. The PDMS-CNT devices continuously measured the contractile stress, beating rate, and beating rhythm of hiPSC-CMs over the entire culturing process, revealing the dynamic evolution of hiPSC-CMs' contractile behaviors. Experimental data showed that cell beating started from day 2, and contractile stress plateaued by day 5. The average contractile stress generated by a monolayer of hiPSC-CMs was determined to be 2.35±0.047 kPa with a beating rate of 1.17±0.068. Five cardiac drugs were applied to hiPSC-CM monolayers, and the effect of each drug at different concentrations was quantified by the device arrays.

TABLE 2

Resistance of nine device elements before and after pre-conditioning

| device element | initial resistance, R (k(2) | resistance after pre-conditioning, Ro (k(2) |
|---|---|---|
| 1 | 96.2 | 68.3 |
| 2 | 123.5 | 79.1 |
| 3 | 105.9 | 69.6 |
| 4 | 311.7 | 94.4 |
| 5 | 152.1 | 86.1 |
| 6 | 173.2 | 76.3 |
| 7 | 243.5 | 92.5 |
| 8 | 201.4 | 84.9 |

REFERENCES (1) Mozaffarian, D.; Benjamin, E. J.; Go, A. S.; Arnett, D. K.; Blaha, M. J.; Cushman, M.; Das, S. R.; Ferranti, S. De; Despres, J. P.; Fullerton, H. J.; Howard, V. J.; Huffman, M. D.; Isasi, C. R.; Jiménez, M. C.; Judd, S. E.; Kissela, B. M.; Lichtman, J. H.; Lisabeth, L. D.; Liu, S.; MacKey, R. H.; Magid, D. J.; McGuire, D. K.; Mohler, E. R.; Moy, C. S.; Muntner, P.; Mussolino, M. E.; Nasir, K.; Neumar, R. W.; Nichol, G.; Palaniappan, L.; Pandey, D. K.; Reeves, M. J.; Rodriguez, C. J.; Rosamond, W.; Sorlie, P. D.; Stein, J.; Towfighi, A.; Turan, T. N.; Virani, S. S.; Woo, D.; Yeh, R. W.; Turner, M. B. Heart Disease and Stroke Statistics-2016 Update a Report from the American Heart Association; 2016; Vol. 133.

(2) Broadley, K. J. The Langendorff Heart Preparation: Reappraisal of Its Role as a Research and Teaching Model for Coronary Vasoactive Drugs. J. Pharmacol. Methods 1979, 2 (2), 143-156.

(3) Yu, J.; Vodyanik, M. A.; Smuga-Otto, K.; Antosiewicz-Bourget, J.; Frane, J. L.; Tian, S.; Nie, J.; Jonsdottir, G. A.; Ruotti, V; Stewart, R.; Slukvin, I. I.; Thomson, J. A. Induced Pluripotent Stem Cell Lines Derived from Human Somatic Cells. Science. 2007, 318 (5858).

(4) Bieling, P.; Li, T.-D.; Weichsel, J.; McGorty, R.; Jreij, P.; Huang, B.; Fletcher, D. A.; Mullins, R. D. Force Feedback Controls Motor Activity and Mechanical Properties of Self-Assembling Branched Actin Networks. Cell 2016, 164 (1-2), 115-127.

(5) Garofalo, F.; Pellegrino, D.; Amelio, D.; Tota, B. The Antarctic Hemoglobinless Icefish, Fifty Five Years Later: A Unique Cardiocirculatory Interplay of Disaptation and Phenotypic Plasticity. Comp. Biochem. Physiol. Part AMol. Integr. Physiol. 2009, 154 (1), 10-28.

(6) Pieske, B.; Kretschmann, B.; Meyer, M.; Holubarsch, C.; Weirich, J.; Posival, H.; Minami, K.; Just, H.; Hasenfuss, G. Alterations in Intracellular Calcium Handling Associated With the Inverse Force-Frequency Relation in Human Dilated Cardiomyopathy. Circulation 1995, 92 (5).

(7) Fu, Y; Westenbroek, R. E.; Scheuer, T.; Catterall, W. A. Basal and β-Adrenergic Regulation of the Cardiac Calcium Channel CaV1.2 Requires Phosphorylation of Serine 1700. Proc. Natl. Acad. Sci. U.S.A 2014, 111 (46), 16598-16603.

(8) Giaever, I.; Keese, C. R. Monitoring Fibroblast Behavior in Tissue Culture with an Applied Electric Field. Proc. Natl. Acad. Sci. U.S.A 1984, 81 (12), 3761-3764.

(9) Xiao, L.; Hu, Z.; Zhang, W.; Wu, C.; Yu, H.; Wang, P. Evaluation of Doxorubicin Toxicity on Cardiomyocytes Using a Dual Functional Extracellular Biochip. Biosens. Bioelectron. 2010, 26 (4), 1493-1499.

(10) Qian, F.; Huang, C.; Lin, Y-D.; Ivanovskaya, A. N.; O'Hara, T. J.; Booth, R. H.; Creek, C. J.; Enright, H. A.; Soscia, D. A.; Belle, A. M.; Liao, R.; Lightstone, F. C.; Kulp, K. S.; Wheeler, E. K. Simultaneous Electrical Recording of Cardiac Electrophysiology and Contraction on Chip. Lab Chip 2017, 17 (10), 1732-1739.

(11) Park, J.; Ryu, J.; Choi, S. K.; Seo, E.; Cha, J. M.; Ryu, S.; Kim, J.; Kim, B.; Lee, S. H. Real-Time Measurement of the Contractile Forces of Self-Organized Cardiomyocytes on Hybrid Biopolymer Microcantilevers. Anal. Chem. 2005, 77 (20), 6571-6580.

(12) Kim, J. Y; Choi, Y S.; Lee, B. K.; Lee, D. W. Surface-Patterned SU-8 Cantilever Arrays for Preliminary Screening of Cardiac Toxicity. Biosens. Bioelectron. 2016, 80, 456-462.

(13) Breugel, H. H. F. I. Van; Bar, P. R. D. Power Density and Exposure Time of He—Ne Laser Irradiation Are More Important Than Total Energy Dose in Photo-Biomodulation of Human Fibroblasts In Vitro. 1992, 537.

(14) Shen, S.; Henry, A.; Tong, J.; Zheng, R.; Chen, G. Polyethylene Nanofibres with Very High Thermal Conductivities. Nat. Nanotechnol. 2010, 5 (4), 251-255.

(15) Wang, Q.-F.; Shen, W.-L.; Liu, C.; Mu, D.-L.; Wu, X.-F.; Guo, N.-G.; Zhu, J.-Q. Effects of Multi-Environmental Factors on Physiological and Biochemical Responses of Large Yellow Croaker, Larimichthys Crocea. Chemosphere 2017, 184, 907-915.

(16) Chung, J. H.; Biesiadecki, B. J.; Ziolo, M. T.; Davis, J. P.; Janssen, P. M. L. Myofilament Calcium Sensitivity: Role in Regulation of in Vivo Cardiac Contraction and Relaxation. Front. Physiol. 2016, 7 (DEC), 1-9.

(17) Gilchrist, K. H.; Giovangrandi, L.; Whittington, R. H.; Kovacs, G. T. A. Sensitivity of Cell-Based Biosensors to Environmental Variables. Biosens. Bioelectron. 2005, 20 (7), 1397-1406.

(18) Lind, J. U.; Busbee, T. A.; Valentine, A. D.; Pasqualini, F. S.; Yuan, H.; Yadid, M.; Park, S.-J.; Kotikian, A.; Nesmith, A. P.; Campbell, P. H.; Vlassak, J. J.; Lewis, J. A.; Parker, K. K. Instrumented Cardiac Microphysiological Devices via Multimaterial Three-Dimensional Printing. Nat. Mater. 2016, 16 (3), 303-308.

(19) Matsudaira, K.; Nguyen, T. V; Shoji, K. H.; Tsukagoshi, T.; Takahata, T.; Shimoyama, I. MEMS Piezoresistive Cantilever for the Direct Measurement of Cardiomyocyte Contractile Force. J. Micromechanics Microengineering 2017, 27 (10).

(20) Trzewik, J.; Artmann-Temiz, A.; Linder, P. T.; Demirci, T.; Digel, I.; Artmann, G. M. Evaluation of Lateral Mechanical Tension in Thin-Film Tissue Constructs. Ann. Biomed. Eng. 2004, 32 (9), 1243-1251.

(21) Polacheck, W. J.; Chen, C. S. Measuring Cell-Generated Forces: A Guide to the Available Tools. Nat. Methods 2016, 13 (5), 415-423.

(22) Goßmann, M.; Frotscher, R.; Linder, P.; Neumann, S.; Bayer, R.; Epple, M.; Staat, M.; Artmann, A.; Artmann, G. M. Mechano-Pharmacological Characterization of Cardiomyocytes Derived from Human Induced Pluripotent Stem Cells. Cell. Physiol. Biochem. 2016, 38 (3), 1182-1198.

(23) Linder, P.; Trzewik, J.; Ruffer, M.; Artmann, G. M.; Digel, I.; Kurz, R.; Rothermel, A.; Robitzki, A.; Temiz Artmann, A. Contractile Tension and Beating Rates of Self-Exciting Monolayers and 3D-Tissue Constructs of Neonatal Rat Cardiomyocytes. Med. Biol. Eng. Comput. 2010, 48 (1), 59-65.

(24) Beussman, K. M.; Rodriguez, M. L.; Leonard, A.; Taparia, N.; Thompson, C. R.; Sniadecki, N. J. Micropost Arrays for Measuring Stem Cell-Derived Cardiomyocyte Contractility. Methods 2016, 94, 43-50.

(25) Han, S. J.; Bielawski, K. S.; Ting, L. H.; Rodriguez, M. L.; Sniadecki, N. J. Decoupling Substrate Stiffness, Spread Area, and Micropost Density: A Close Spatial Relationship between Traction Forces and Focal Adhesions. Biophys. J. 2012, 103 (4), 640-648.

(26) Plotnikov, S. V; Sabass, B.; Schwarz, U. S.; Waterman, C. M. High-Resolution Traction Force Microscopy, 1st ed.; Elsevier Inc., 2014; Vol. 123.

(27) Munevar, S.; Wang, Y; Dembo, M. Traction Force Microscopy of Migrating Normal and H-Ras Transformed 3T3 Fibroblasts. Biophys. J. 2001, 80 (4), 1744-1757.

(28) Mierke, C. T., Rosel, D., Fabry, B., & Brábek, J. Contractile Forces in Tumor Cell Migration. Eur. J. Cell Biol. 2008, 87 (8-9), 669-676.

(29) Wu, Y N.; Law, J. B. K.; He, A. Y; Low, H. Y; Hui, J. H. P.; Lim, C. T.; Yang, Z.; Lee, E. H. Substrate Topography Determines the Fate of Chondrogenesis from Human Mesenchymal Stem Cells Resulting in Specific Cartilage Phenotype Formation. Nanomedicine Nanotechnology, Biol. Med. 2014, 10 (7), 1507-1516.

(30) del Alamo, J. C.; Lemons, D.; Serrano, R.; Savchenko, A.; Cerignoli, F.; Bodmer, R.; Mercola, M. High Throughput Physiological Screening of iPSC-Derived Cardiomyocytes for Drug Development. Biochim. Biophys. Acta—Mol. Cell Res. 2016, 1863 (7), 1717-1727.

(31) Klein, C. A. How Accurate Are Stoney's Equation and Recent Modifications. J. Appl. Phys. 2000, 88 (9), 5487-5489.

(32) Nguyen, T. K.; Lee, D. W.; Lee, B. K. Numerical Investigation of Perforated Polymer Microcantilever Sensor for Contractile Behavior of Cardiomyocytes. Jpn. J. Appl. Phys. 2017, 56 (6).

(33) Liu, X.; Zhao, H.; Lu, Y; Li, S.; Lin, L.; Du, Y; Wang, X. In Vitro Cardiomyocyte-Driven Biogenerator Based on Aligned Piezoelectric Nanofibers. Nanoscale 2016, 8 (13), 7278-7286.

(34) Spaepen, F. Interfaces and Stresses in Thin Films. Acta Mater. 2000, 48 (1), 31-42.

(35) Miquelard-Garnier, G.; Zimberlin, J. A.; Sikora, C. B.; Wadsworth, P.; Crosby, A. J. Polymer Microlenses for Quantifying Cell Sheet Mechanics. Soft Matter 2010, 6 (2), 398.

(36) Merkel, T. C.; Bondar, V. I.; Nagai, K.; Freeman, B. D.; Pinnau, I. Gas Sorption, Diffusion, and Permeation in Poly(dimethylsiloxane). J. Polym. Sci. Part B Polym. Phys. 2000, 38 (3), 415-434.

(37) Firpo, G.; Angeli, E.; Repetto, L.; Valbusa, U. Permeability Thickness Dependence of Polydimethylsiloxane (PDMS) Membranes. J. Memb. Sci. 2015, 481, 1-8.

(38) Gaietta, Guido, Thomas J. Deerinck, Stephen R. Adams, James Bouwer, Oded Tour, Dale W. Laird, Gina E. Sosinsky, Roger Y Tsien, and Mark H. Ellisman. Multicolor and Electron Microscopic Imaging of Connexin Trafficking. Science. 2002, 296 (5567), 503-507.

(39) Huikuri, H. V; Seppanen, T.; Koistinen, M. J.; Airaksinen, J.; Ikaheimo, M. J.; Castellanos, a; Myerburg, R. J. Abnormalities in Beat-to-Beat Dynamics of Heart Rate before the Spontaneous Onset of Life-Threatening Ventricular Tachyarrhythmias in Patients with Prior Myocardial Infarction. Circulation 1996, 93 (10), 1836-1844.

(40) Bers, D. M. Cardiac Excitation-Contraction Coupling. Nature 2002, 415 (6868), 198-205.

(41) Lymperopoulos, A.; Rengo, G.; Koch, W. J. Adrenergic Nervous System in Heart Failure: Pathophysiology and Therapy. Circ. Res. 2013, 113 (6), 739-753. [0191](42) Tanaka, T.; Tohyama, S.; Murata, M.; Nomura, F.; Kaneko, T.; Chen, H.; Hattori, F.; Egashira, T.; Seki, T.; Ohno, Y; Koshimizu, U.; Yuasa, S.; Ogawa, S.; Yamanaka, S.; Yasuda, K.; Fukuda, K. In Vitro Pharmacologic Testing Using Human Induced Pluripotent Stem Cell-Derived Cardiomyocytes. Biochem. Biophys. Res. Commun. 2009, 385 (4), 497-502.

(43) Liu, L. C. Y; Dorhout, B.; van der Meer, P.; Teerlink, J. R.; Voors, A. A. Omecamtiv Mecarbil: A New Cardiac Myosin Activator for the Treatment of Heart Failure. Expert Opin. Investig. Drugs 2015, 25 (1), 117-127.

(44) Casini, S.; Verkerk, A. O.; Remme, C. A. Human iPSC-Derived Cardiomyocytes for Investigation of Disease Mechanisms and Therapeutic Strategies in Inherited Arrhythmia Syndromes: Strengths and Limitations. Cardiovasc. Drugs Ther. 2017, 31 (3), 325-344.

(45) Matsuo, J.; Nakamura, Y; Izumi-Nakaseko, H.; Ando, K.; Sekino, Y; Sugiyama, A. Possible Effects of Inhibition of IKr and IKs on Field-Potential Waveforms in the Human iPS Cell-Derived Cardiomyocytes Sheet. J. Pharmacol. Sci. 2015, 128 (2), 92-95.

(46) Hayakawa, T.; Kunihiro, T.; Ando, T.; Kobayashi, S.; Matsui, E.; Yada, H.; Kanda, Y; Kurokawa, J.; Furukawa, T. Image-Based Evaluation of Contraction-Relaxation Kinetics of Human-Induced Pluripotent Stem Cell-Derived Cardiomyocytes: Correlation and Complementarity with Extracellular Electrophysiology. J. Mol. Cell. Cardiol. 2014, 77, 178-191.

(47) So, H. M.; Sim, J. W.; Kwon, J.; Yun, J.; Baik, S.; Chang, W. S. Carbon Nanotube Based Pressure Sensor for Flexible Electronics. Mater. Res. Bull. 2013, 48 (12), 5036-5039.

(48) Cai, L.; Song, L.; Luan, P.; Zhang, Q.; Zhang, N.; Gao, Q.; Zhao, D.; Zhang, X.; Tu, M.; Yang, F.; Zhou, W.; Fan, Q.; Luo, J.; Zhou, W.; Ajayan, P. M.; Xie, S. Super-Stretchable, Transparent Carbon Nanotube-Based Capacitive Strain Sensors for Human Motion Detection. Sci. Rep. 2013, 3, 1-9.

(49) Ladeira, M. S.; Andrade, V. A.; Gomes, E. R. M.; Aguiar, C. J.; Moraes, E. R.; Soares, J. S.; Silva, E. E.; Lacerda, R. G.; Ladeira, L. O.; Jorio, A.; Lima, P.; Fatima Leite, M.; Resende, R. R.; Guatimosim, S. Highly Efficient siRNA Delivery System into Human and Murine Cells Using Single-Wall Carbon Nanotubes. Nanotechnology 2010, 21 (38).

(50) Hazeltine, L. B.; Simmons, C. S.; Salick, M. R.; Lian, X.; Badur, M. G.; Han, W.; Delgado, S. M.; Wakatsuki, T.; Crone, W. C.; Pruitt, B. L.; Palecek, S. P. Effects of Substrate Mechanics on Contractility of Cardiomyocytes Generated from Human Pluripotent Stem Cells. Int. J. Cell Biol. 2012, 2012.

(51) Hersch, N.; Wolters, B.; Dreissen, G.; Springer, R.; Kirchgeßner, N.; Merkel, R.; Hoffmann, B. The Constant Beat: Cardiomyocytes Adapt Their Forces by Equal Contraction upon Environmental Stiffening. Biol. Open 2013, 2 (3), 351-361.

(52) Broughton, K. M.; Russell, B. Cardiomyocyte Subdomain Contractility Arising from Microenvironmental Stiffness and Topography. Biomech. Model. Mechanobiol. 2015, 14 (3), 589-602.

(53) Rajagopalan, J.; Taher, M.; Saif, A. MEMS Sensors and Microsystems for Cell Mechanobiology. J. Micromech. Microeng 2011, 21, 54002-54011.

(54) Mordina, B.; Tiwari, R. K.; Setua, D. K.; Sharma, A. Superior Elastomeric Nanocomposites with Electrospun Nanofibers and Nanoparticles of CoFe 2 O 4 for Magnetorheological Applications. RSC Adv. 2015, 5 (25), 19091-19105.

(55) Pimentel, D. M.; Oliveira, F. M. De; Luz, R. C. S. Development of a Selective and Sensitive Sensor for Urate Determination Based on Tris(1,10-phenantroline) copper(II) Bis(tetracyanoquinodimethanide) Adsorbed on Carbon Nanotubes. 2015, 26 (10), 2035-2045.

(56) Pesl, M.; Pribyl, J.; Acimovic, I.; Vilotic, A.; Jelinkova, S.; Salykin, A.; Lacampagne, A.; Dvorak, P.; Meli, A. C.; Skladal, P.; Rotrekl, V. Atomic Force Microscopy Combined with Human Pluripotent Stem Cell Derived Cardiomyocytes for Biomechanical Sensing. Biosens. Bioelectron. 2016, 85, 751-757.

(57) Huebsch, N.; Loskill, P.; Deveshwar, N.; Spencer, C. I.; Judge, L. M.; Mandegar, M. A.; B. Fox, C.; Mohamed, T. M. A.; Ma, Z.; Mathur, A.; Sheehan, A. M.; Truong, A.; Saxton, M.; Yoo, J.; Srivastava, D.; Desai, T. A.; So, P.-L.; Healy, K. E.; Conklin, B. R. Miniaturized iPS-Cell-Derived Cardiac Muscles for Physiologically Relevant Drug Response Analyses. Sci. Rep. 2016, 6 (April), 24726.

(58) Huebsch, N.; Loskill, P.; Deveshwar, N.; Spencer, C. I.; Judge, L. M.; Mandegar, M. A.; B. Fox, C.; Mohamed, T. M. A.; Ma, Z.; Mathur, A.; Sheehan, A. M.; Truong, A.; Saxton, M.; Yoo, J.; Srivastava, D.; Desai, T. A.; So, P.-L.; Healy, K. E.; Conklin, B. R. Miniaturized iPS-Cell-Derived Cardiac Muscles for Physiologically Relevant Drug Response Analyses. Sci. Rep. 2016, 6 (1), 24726.

(59) Gaitas, A.; Malhotra, R.; Li, T.; Herron, T.; Jalife, J. A Device for Rapid and Quantitative Measurement of Cardiac Myocyte Contractility. Rev. Sci. Instrum. 2015, 86 (3).

(60) Dai, Y; Oyunbaatar, N. E.; Lee, B. K.; Kim, E. S.; Lee, D. W. Spiral-Shaped SU-8 Cantilevers for Monitoring Mechanical Response of Cardiomyocytes Treated with Cardiac Drugs. Sensors Actuators, B Chem. 2017.

(61) Ribeiro, A. J. S.; Schwab, O.; Mandegar, M. A.; Ang, Y S.; Conklin, B. R.; Srivastava, D.; Pruitt, B. L. Multi-Imaging Method to Assay the Contractile Mechanical Output of Micropatterned Human iPSC-Derived Cardiac Myocytes. Circ. Res. 2017, 120 (10), 1572-1583.

(62) Devalla, H. D.; Schwach, V.; Ford, J. W.; Milnes, J. T.; El-Haou, S.; Jackson, C.; Gkatzis, K.; Elliott, D. A.; Chuva de Sousa Lopes, S. M.; Mummery, C. L.; Verkerk, A. O.; Passier, R. Atrial-like Cardiomyocytes from Human Pluripotent Stem Cells Are a Robust Preclinical Model for Assessing Atrial-Selective Pharmacology. EMBO Mol. Med. 2015, 7 (4), 394-410.

(63) You, J.; Moon, H.; Lee, B. Y; Jin, J. Y; Chang, Z. E.; Kim, S. Y; Park, J.; Hwang, Y S.; Kim, J. Cardiomyocyte Sensor Responsive to Changes in Physical and Chemical Environments. J. Biomech. 2014, 47 (2), 400-409.

(64) Nakamura, Y; Matsuo, J.; Miyamoto, N.; Ojima, A.; Ando, K.; Kanda, Y; Sawada, K.; Sugiyama, A.; Sekino, Y. Assessment of Testing Methods for Drug-Induced Repolarization Delay and Arrhythmias in an iPS Cell-Derived Cardiomyocyte Sheet: Multi-Site Validation Study. J. Pharmacol. Sci. 2014, 124 (4), 494-501.

(65) Ken'ei Matsudaira, Thanh-Vinh Nguyen, Kayoko Hirayama Shoji, Takuya Tsukagoshi, T. T. and I. S. MEMS FORCE SENSOR ARRAY FOR EVALUATING THE CONTRACTILITY OF IPS CELL-DERIVED CARDIOMYOCYTES Ken'Ei Matsudaira, Thanh-Vinh Nguyen, Kayoko Hirayama Shoji, The University of Tokyo, Tokyo, JAPAN. 2017, 36-38.

(66) Kim, D. S.; Jeong, Y J.; Lee, B. K.; Shanmugasundaram, A.; Lee, D. W. Piezoresistive Sensor-Integrated PDMS Cantilever: A New Class of Device for Measuring the Drug-Induced Changes in the Mechanical Activity of Cardiomyocytes. Sensors Actuators, B Chem. 2017, 240, 566-572.

(67) Wu, W. Y; Zhong, X.; Wang, W.; Miao, Q.; Zhu, J. J. Flexible PDMS-Based Three-Electrode Sensor. Electrochem. commun. 2010, 12 (11), 1600-1604).

(68) Xiao, S. Y; Che, L. F.; Li, X. X.; Wang, Y. L. A Novel Fabrication Process of MEMS Devices on Polyimide Flexible Substrates. Microelectron. Eng. 2008, 85 (2), 452-457.

(69) Park, H.; Kim, K. H.; Yoon, J.; Kim, K. K.; Park, S. M.; Ha, J. S. Fabrication of Patterned Flexible Graphene Devices via Facile Direct Transfer of as-Grown Bi-Layer Graphene. Appl. Surf. Sci. 2015, 328, 235-240.

Figure 17:
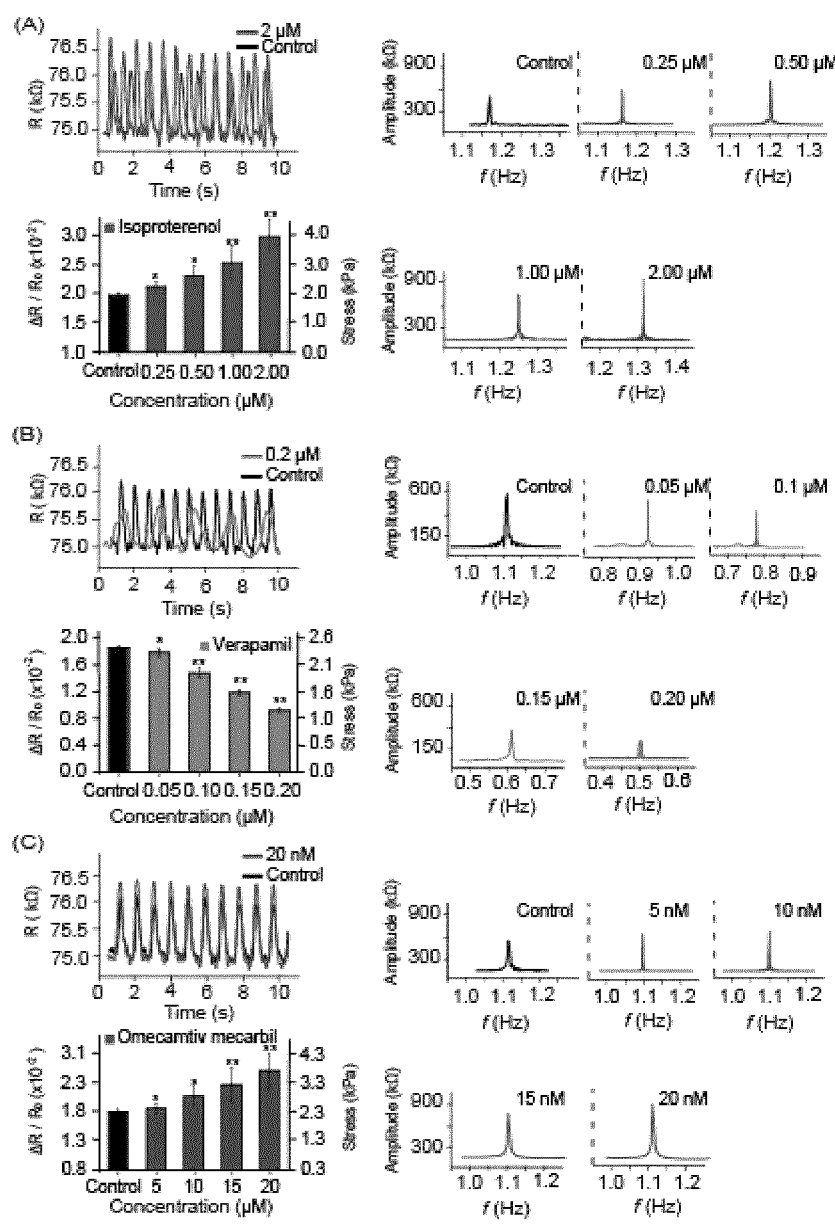
FIG. 17 Platform validation with five kinds of drugs (A-E). Each drug was tested in four increasing concentrations on day ten. Data were measured prior to drug treatment acted as the control group. Resistance wave and beating rhythm were plotted under maximal drug concentration and were compared to pre-drug condition. Changes in $\Delta R/R_0$, contractile stress, beating rate and rhythm showed dose-dependent effects of five drugs on hiPSC-CM monolayers. (*, P<0.05; **, P<0.005). (F) Poincare plot for the beating rhythm analysis in the presence of five different drugs. (G) Mechanism of "cardiomyocyte excitation-contraction coupling" process. Drugs influenced cell beating behaviors by regulating particular receptors in this process. βAR, β-adrenergic receptor; RyR2, ryanodine receptor 2; LTCC, L-type calcium channel; SERCA, sarcoplasmic/endoplasmic reticulum $Ca^{2+}$-ATPase.
Figure 17:
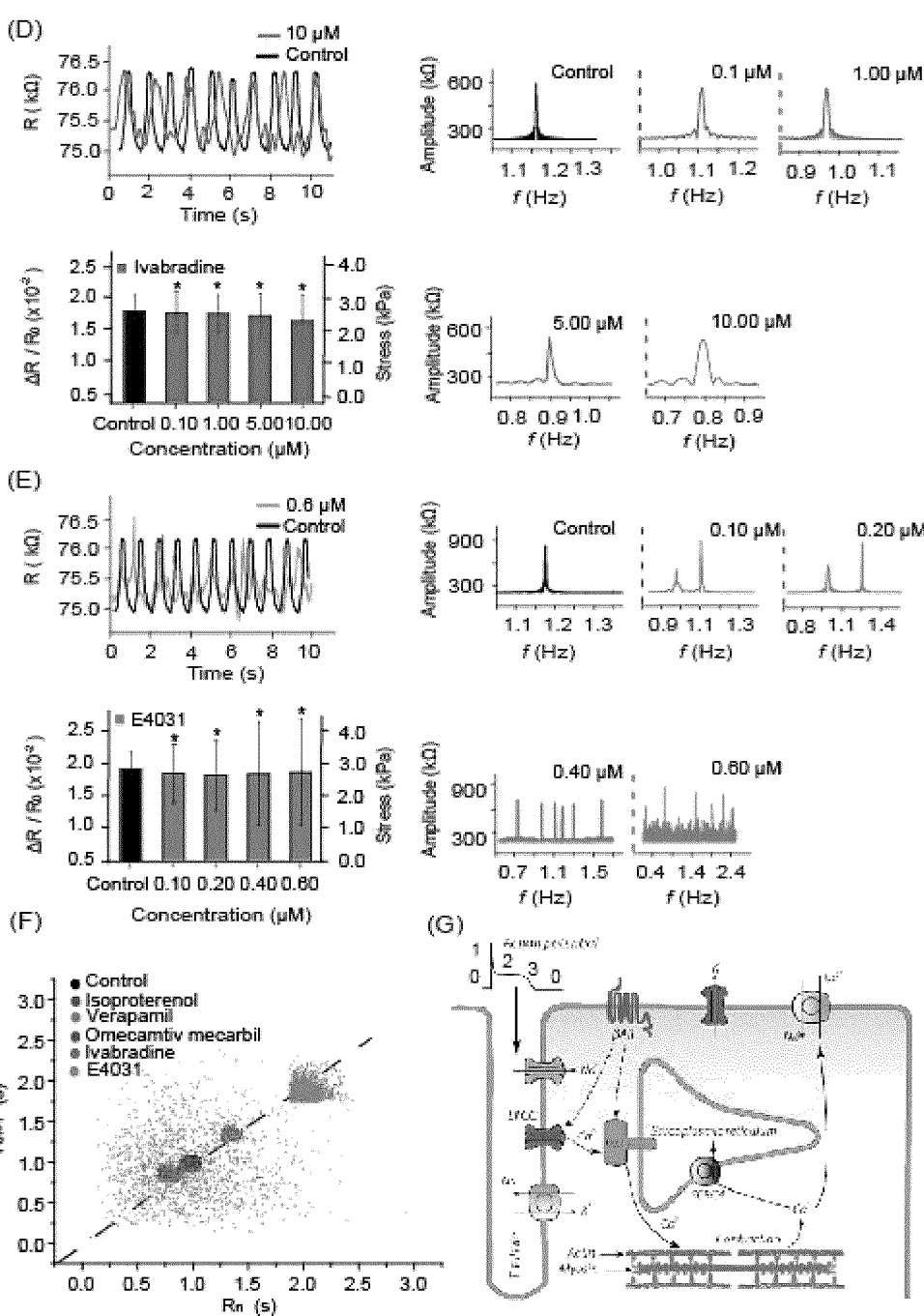

REFERENCES FOUND IN THE TABLES,
DESCRIPTION OF FIG. 17 AND
CARDIOMYOCYTE CONTRACTILE STRESS
ANALYSIS

[1] C. A. Klein, "How accurate are Stoney's equation and recent modifications," J. Appl. Phys., vol. 88, no. 9, pp. 5487-5489, 2000.

[2] G. Miquelard-Garnier, J. A. Zimberlin, C. B. Sikora, P. Wadsworth, and A. J. Crosby, "Polymer microlenses for quantifying cell sheet mechanics," Soft Matter, vol. 6, no. 2, p. 398, 2010.

[3] K. Wilson, M. Das, K. J. Wahl, R. J. Colton, and J. Hickman, "Measurement of contractile stress generated by cultured rat muscle on silicon cantilevers for toxin detection and muscle performance enhancement," PLoS One, vol. 5, no. 6, 2010.

[4] P. Class, "Polymer Data," October, p. 1264, 1999.

[5] J. Wegener, S. Zink, P. Rösen, and H. Galla, "Use of electrochemical impedance measurements to monitor beta-adrenergic stimulation of bovine aortic endothelial cells.," Pflugers Arch., vol. 437, no. 6, pp. 925-34, 1999.

[6] M. K. B. Jonsson, Q.-D. Wang, and B. Becker, "Impedance-based detection of beating rhythm and proarrhythmic effects of compounds on stem cell-derived cardiomyocytes.," Assay Drug Dev. Technol., vol. 9, no. 6, pp. 589-599, 2011.

[7] L. Xiao, Z. Hu, W. Zhang, C. Wu, H. Yu, and P. Wang, "Evaluation of doxorubicin toxicity on cardiomyocytes using a dual functional extracellular biochip," Biosens. Bioelectron., vol. 26, no. 4, pp. 1493-1499, 2010.

[8] T. Boudou et al., "A microfabricated platform to measure and manipulate the mechanics of engineered cardiac microtissues.," Tissue Eng. Part A, vol. 18, no. 9-10, pp. 910-9, 2012.

[9] N. L. Francis, N. K. Bennett, A. Halikere, Z. P. Pang, and P. V. Moghe, "Self-Assembling Peptide Nanofiber Scaffolds for 3-D Reprogramming and Transplantation of Human Pluripotent Stem Cell-Derived Neurons," ACS Biomater. Sci. Eng., vol. 2, no. 6, pp. 1030-1038, 2016.

[10] C. Denning et al., "Cardiomyocytes from human pluripotent stem cells: From laboratory curiosity to industrial biomedical platform," Biochim. Biophys. Acta—Mol. Cell Res., vol. 1863, no. 7, pp. 1728-1748, 2016.

[11] K. M. Beussman, M. L. Rodriguez, A. Leonard, N. Taparia, C. R. Thompson, and N. J. Sniadecki, "Micropost arrays for measuring stem cell-derived cardiomyocyte contractility," Methods, vol. 94, pp. 43-50, 2016.

[12] M. L. Rodriguez, B. T. Graham, L. M. Pabon, S. J. Han, C. E. Murry, and N. J. Sniadecki, "Measuring the contractile forces of human induced pluripotent stem cell-derived cardiomyocytes with arrays of microposts.," J. Biomech. Eng., vol. 136, no. 5, p. 51005, 2014.

[13] J. Fu et al., "Mechanical regulation of cell function with geometrically modulated elastomeric substrates," Nat Methods, vol. 7, no. 9, pp. 733-736, 2010.

[14] L. B. Hazeltine et al., "Effects of substrate mechanics on contractility of cardiomyocytes generated from human pluripotent stem cells," Int. J. Cell Biol., vol. 2012, 2012.

[15] S. V. Plotnikov, B. Sabass, U. S. Schwarz, and C. M. Waterman, High-Resolution Traction Force Microscopy, 1st ed., vol. 123. Elsevier Inc., 2014.

[16] A. Marinkovic, J. D. Mih, J. A. Park, F. Liu, and D. J. Tschumperlin, "Improved throughput traction microscopy reveals pivotal role for matrix stiffness in fibroblast contractility and TGF-beta responsiveness," Am. J. Physiol. Lung Cell. Mol. Physiol., vol. 303, no. 3, pp. L169-80, 2012.

[17] J. G. Jacot, A. D. McCulloch, and J. H. Omens, "Substrate stiffness affects the functional maturation of neonatal rat ventricular myocytes.," Biophys. J., vol. 95, no. 7, pp. 3479-87, 2008.

[18] S. Sugiura, S. Nishimura, S. Yasuda, Y Hosoya, and K. Katoh, "Carbon fiber technique for the investigation of single-cell mechanics in intact cardiac myocytes.," Nat. Protoc., vol. 1, no. 3, pp. 1453-7, 2006.

[19] G. Iribe, M. Helmes, and P. Kohl, "Force-length relations in isolated intact cardiomyocytes subjected to dynamic changes in mechanical load.," Am. J. Physiol. Heart Circ. Physiol., vol. 292, no. 3, pp. H1487-97, 2007.

[20] M. Goßmann et al., "Mechano-pharmacological characterization of cardiomyocytes derived from human induced pluripotent stem cells," Cell. Physiol. Biochem., vol. 38, no. 3, pp. 1182-1198, 2016.

[21] J. Trzewik, A. Artmann-Temiz, P. T. Linder, T. Demirci, I. Digel, and G. M. Artmann, "Evaluation of lateral mechanical tension in thin-film tissue constructs," Ann. Biomed. Eng., vol. 32, no. 9, pp. 1243-1251, 2004.

[22] J. Park et al., "Real-time measurement of the contractile forces of self-organized cardiomyocytes on hybrid biopolymer microcantilevers," Anal. Chem., vol. 77, no. 20, pp. 6571-6580, 2005.

[23] M. Pesl et al., "Atomic force microscopy combined with human pluripotent stem cell derived cardiomyocytes for biomechanical sensing," Biosens. Bioelectron., vol. 85, pp. 751-757, 2016.

[24] P. A. Galie, F. J. Byfield, C. S. Chen, J. Y Kresh, and P. A. Janmey, "Mechanically stimulated contraction of engineered cardiac constructs using a microcantilever," IEEE Trans. Biomed. Eng., vol. 62, no. 2, pp. 438-442, 2015.

[25] Y Tanaka et al., "An actuated pump on-chip powered by cultured cardiomyocytes," Lab Chip, vol. 6, no. 3, p. 362, 2006.

Aspects described herein can be embodied in other forms and combinations without departing from the spirit or essential attributes thereof. Thus, it will of course be understood that embodiments are not limited to the specific details described herein, which are given by way of example only, and that various modifications and alterations are possible.

Through the embodiments that are illustrated and described, the currently contemplated best mode of making and using the invention is described. Without further elaboration, it is believed that one of ordinary skill in the art can, based on the description presented herein, utilize the present invention to the full extent. Future applications claiming priority to this application may or may not include the following claims, and may include claims broader, narrower, or entirely different from the following claims.

What is claimed is:

1. A device for measuring at least one cellular activity comprising: (a) a deformable polymeric base membrane having a first side and a second side, the polymeric base including a well, the well having an opening on the first side, a cavity extending from the opening and a floor formed by the second side of the polymeric base membrane, (b) a deformable polymeric top membrane overlapping the second side of the polymeric base membrane; and (c) a sensing element for measuring the at least one cellular activity disposed between the polymeric base membrane and the polymeric top membrane, the sensing element being disposed over the floor of the well, such that a portion of the second side that forms the floor of the well, the sensing element and a portion of the top membrane that overlaps the well form a suspended membrane.

2. The device of claim 1, wherein the device further includes a substrate, and wherein the first side of the polymeric base membrane is connected to the substrate.

3. The device of claim 1, wherein the polymeric base membrane further includes a hole configured to receive a tubing means, and microchannels connecting the well with the hole.

4. The device of claim 1, wherein the device further includes a polymeric ring coupled onto the portion of the top polymeric membrane that forms the suspended membrane.

5. The device of claim 1, wherein the device further includes an impedance spectroscope, the impedance spectroscope measuring an electrical resistance of the sensing element.

6. The device of claim 1, wherein the top polymeric membrane further includes embedded beads capable of producing an optical signal.

7. The device of claim 6, wherein the embedded beads are fluorescent beads.

8. The device of claim 1, wherein the device includes more than one well and more than one sensing element, each sensing element being disposed over the floor of one well, such that a portion of the second side that forms the floor of the well, the sensing element and a portion of the top membrane that overlaps the well form a number of suspended membranes equal to the number of wells in the device.

9. The device of claim 1, wherein the sensing element is selected from a carbon nanotube (CNT) sensing element, a gold-based sensing element, a platinum-based sensing element, a carbon ink-based sensing element or a graphene-based sensing element.

10. The device of claim 1, wherein the sensing element is a carbon nanotube (CNT) strip, wherein the CNT strip extends over the floor of the well.

11. A method for continuous measuring at least one cellular activity, comprising:
   (a) providing a device according to claim 1;
   (b) seeding cells onto the suspended membrane of the device; and
   (c) continuously measuring an electrical resistance of the sensing element, thereby continuously measuring the cellular activity of the cells.

12. A method for determining an effect of at least one drug on at least one cellular activity comprising:
   (a) providing a device according to claim 1;
   (b) seeding cells onto the suspended membrane of the device,
   (c) exposing the cells either before or after being seeded to the at least one drug,
   (d) continuously measuring an electrical resistance of the sensing element, thereby determining the effect of the at least one drug on the least one cellular activity of the cells.

13. The method of claim 11, wherein the cellular activity is contractility, beating rate or beating rhythm.

14. The method of claim 11, wherein the seeded cells are cardiomyocytes.

\* \* \* \* \*